(12) United States Patent
Hyde

(10) Patent No.: US 7,740,638 B2
(45) Date of Patent: *Jun. 22, 2010

(54) APPARATUSES AND METHODS FOR HEART VALVE REPAIR

(75) Inventor: Gregory Mathew Hyde, Menlo Park, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 256 days.

This patent is subject to a terminal disclaimer.

(21) Appl. No.: 11/553,105

(22) Filed: Oct. 26, 2006

(65) Prior Publication Data

US 2007/0050019 A1    Mar. 1, 2007

Related U.S. Application Data

(60) Continuation of application No. 11/240,589, filed on Sep. 29, 2005, which is a division of application No. 10/272,060, filed on Oct. 15, 2002, now Pat. No. 7,087,064.

(51) Int. Cl.
*A61B 17/10* (2006.01)

(52) U.S. Cl. .................. 606/139; 606/142; 606/144; 606/232

(58) Field of Classification Search ............. 606/72, 606/73, 139, 144, 228, 232, 99, 104, 142, 606/143, 148, 300, 304, 311, 312, 325, 151

See application file for complete search history.

(56) References Cited

U.S. PATENT DOCUMENTS 3,177,543 A    4/1965    Fountain

| 3,716,058 A | 2/1973 | Tanner, Jr. |
| 4,128,100 A | 12/1978 | Wendorff |
| 4,719,924 A | 1/1988 | Crittenden et al. |
| 4,781,186 A | 11/1988 | Simpson et al. |
| 4,817,250 A | 4/1989 | Kurosaki |

(Continued)

FOREIGN PATENT DOCUMENTS

DE    10161543 A1    6/2003

(Continued)

OTHER PUBLICATIONS

Bonow, R., et al., "Guidelines for the Management of Patients with Valvular Health Disease," Report of American College of Cardiology/American Heart Assoc. Task Force on Practice Guidelines (Committee on Management of Patients with Valvular Heart Disease), American College of Cardiology and American Heart Assoc., Inc., 1998, pp. 1949-1984.

(Continued)

*Primary Examiner*—Darwin P Erezo
(74) *Attorney, Agent, or Firm*—Jonathan Feuchtwang; Blakely Sokoloff Taylor & Zafman LLP

(57) ABSTRACT

A medical device for treating a heart having a faulty heart valve is disclosed. The medical device comprises a ligature including a first anchoring member and a second anchoring member is used. The ligature is percutaneously deployable into a patient with a faulty heart valve wherein the first anchoring member to anchor to a first tissue area of the heart and the second anchoring member to anchor to a second tissue area of the heart.

14 Claims, 16 Drawing Sheets

U.S. PATENT DOCUMENTS

| | | | |
|---|---|---|---|
| 4,830,023 A | 5/1989 | de Toledo et al. | |
| 4,920,980 A | 5/1990 | Jackowski | |
| 4,927,421 A * | 5/1990 | Goble et al. | 606/73 |
| 4,994,067 A | 2/1991 | Summers | |
| 5,040,548 A | 8/1991 | Yock | |
| 5,061,273 A | 10/1991 | Yock | |
| 5,100,418 A | 3/1992 | Yoon et al. | |
| 5,100,421 A * | 3/1992 | Christoudias | 606/147 |
| 5,102,421 A * | 4/1992 | Anspach, Jr. | 606/232 |
| 5,116,337 A * | 5/1992 | Johnson | 606/73 |
| 5,129,902 A * | 7/1992 | Goble et al. | 606/65 |
| 5,141,520 A * | 8/1992 | Goble et al. | 606/232 |
| 5,156,616 A * | 10/1992 | Meadows et al. | 606/232 |
| 5,171,233 A | 12/1992 | Amplatz et al. | |
| 5,201,598 A | 4/1993 | Tehan | |
| 5,234,443 A * | 8/1993 | Phan et al. | 606/148 |
| 5,242,456 A | 9/1993 | Nash et al. | |
| 5,246,441 A * | 9/1993 | Ross et al. | 606/53 |
| 5,350,395 A | 9/1994 | Yock | |
| 5,358,479 A | 10/1994 | Wilson | |
| 5,370,662 A * | 12/1994 | Stone et al. | 606/232 |
| 5,374,275 A * | 12/1994 | Bradley et al. | 606/144 |
| 5,383,260 A | 1/1995 | Deschenes et al. | |
| 5,431,673 A | 7/1995 | Summers et al. | |
| 5,441,483 A | 8/1995 | Avitall | |
| 5,451,233 A | 9/1995 | Yock | |
| 5,456,667 A | 10/1995 | Ham et al. | |
| 5,487,757 A | 1/1996 | Truckai et al. | |
| 5,495,974 A | 3/1996 | Deschenes et al. | |
| 5,518,162 A | 5/1996 | Deschenes et al. | |
| 5,522,873 A | 6/1996 | Jackman et al. | |
| 5,531,686 A | 7/1996 | Lundquist et al. | |
| 5,554,184 A | 9/1996 | Machiraju | |
| 5,569,277 A | 10/1996 | Evans et al. | |
| 5,571,215 A | 11/1996 | Sterman et al. | |
| 5,588,188 A | 12/1996 | Jermyn, Jr. | |
| 5,609,598 A | 3/1997 | Laufer et al. | |
| 5,613,937 A | 3/1997 | Garrison et al. | |
| 5,617,854 A | 4/1997 | Munsif | |
| 5,626,613 A * | 5/1997 | Schmieding | 606/232 |
| 5,632,754 A | 5/1997 | Farley et al. | |
| 5,640,955 A | 6/1997 | Ockuly et al. | |
| 5,642,736 A | 7/1997 | Avitall | |
| 5,681,280 A | 10/1997 | Rusk et al. | |
| 5,681,346 A | 10/1997 | Orth et al. | |
| 5,682,906 A | 11/1997 | Sterman et al. | |
| 5,687,723 A | 11/1997 | Avitall | |
| 5,728,129 A | 3/1998 | Summers | |
| 5,782,828 A | 7/1998 | Chen et al. | |
| 5,810,882 A | 9/1998 | Bolduc et al. | |
| 5,823,955 A | 10/1998 | Kuck et al. | |
| 5,824,008 A | 10/1998 | Bolduc et al. | |
| 5,865,800 A | 2/1999 | Mirarchi et al. | |
| 5,868,733 A | 2/1999 | Ockuly et al. | |
| 5,868,767 A | 2/1999 | Farley et al. | |
| 5,916,213 A | 6/1999 | Haissaguerre et al. | |
| 5,954,731 A * | 9/1999 | Yoon | 606/144 |
| 5,961,440 A | 10/1999 | Schweich, Jr. et al. | |
| 5,964,772 A | 10/1999 | Bolduch et al. | |
| 5,972,022 A | 10/1999 | Huxel | |
| 5,989,284 A | 11/1999 | Laufer | |
| 6,001,095 A | 12/1999 | de la Rama et al. | |
| 6,001,104 A | 12/1999 | Benderev et al. | |
| 6,001,127 A | 12/1999 | Schoon et al. | |
| 6,004,332 A | 12/1999 | Yoon et al. | |
| 6,017,358 A * | 1/2000 | Yoon et al. | 606/205 |
| 6,021,340 A | 2/2000 | Randolph et al. | |
| 6,027,514 A | 2/2000 | Stine | |
| 6,036,715 A | 3/2000 | Yock | |
| 6,045,497 A | 4/2000 | Schweich, Jr. et al. | |
| 6,050,936 A | 4/2000 | Schweich, Jr. et al. | |
| 6,051,008 A | 4/2000 | Saadat et al. | |
| 6,059,715 A | 5/2000 | Schweich, Jr. et al. | |
| 6,077,214 A | 6/2000 | Mortier et al. | |
| 6,090,096 A | 7/2000 | St. Goar et al. | |
| 6,093,199 A | 7/2000 | Brown et al. | |
| 6,110,100 A | 8/2000 | Talpade | |
| 6,113,609 A | 9/2000 | Adams | |
| 6,117,176 A | 9/2000 | Chen | |
| 6,120,520 A | 9/2000 | Saadat et al. | |
| 6,123,699 A | 9/2000 | Webster, Jr. | |
| 6,149,669 A * | 11/2000 | Li | 606/232 |
| 6,161,543 A | 12/2000 | Cox et al. | |
| 6,162,168 A | 12/2000 | Schweich, Jr. et al. | |
| 6,164,283 A | 12/2000 | Lesh | |
| 6,165,119 A | 12/2000 | Schweich, Jr. et al. | |
| 6,165,120 A | 12/2000 | Schweich, Jr. et al. | |
| 6,165,164 A | 12/2000 | Hill et al. | |
| 6,165,183 A | 12/2000 | Kuehn et al. | |
| 6,165,197 A | 12/2000 | Yock | |
| 6,174,323 B1 | 1/2001 | Biggs et al. | |
| 6,176,240 B1 | 1/2001 | Nikolchev et al. | |
| 6,178,346 B1 | 1/2001 | Amundson et al. | |
| 6,182,664 B1 | 2/2001 | Cosgrove | |
| 6,183,411 B1 | 2/2001 | Mortier et al. | |
| 6,187,040 B1 | 2/2001 | Wright | |
| 6,190,401 B1 * | 2/2001 | Green et al. | 606/224 |
| 6,190,408 B1 | 2/2001 | Melvin | |
| 6,203,531 B1 | 3/2001 | Ockuly et al. | |
| 6,210,407 B1 | 4/2001 | Webster, Jr. | |
| 6,210,432 B1 | 4/2001 | Solem | |
| 6,231,561 B1 * | 5/2001 | Frazier et al. | 604/500 |
| 6,231,587 B1 | 5/2001 | Makower | |
| 6,241,728 B1 | 6/2001 | Gaiser et al. | |
| 6,254,568 B1 | 7/2001 | Ponzi | |
| 6,254,598 B1 | 7/2001 | Edwards et al. | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,267,781 B1 | 7/2001 | Tu | |
| 6,269,819 B1 | 8/2001 | Oz et al. | |
| 6,270,526 B1 | 8/2001 | Cox | |
| 6,283,127 B1 | 9/2001 | Sterman et al. | |
| 6,283,962 B1 | 9/2001 | Tu et al. | |
| 6,299,622 B1 | 10/2001 | Snow et al. | |
| 6,306,133 B1 | 10/2001 | Tu et al. | |
| 6,312,447 B1 | 11/2001 | Grimes | |
| 6,325,823 B1 | 12/2001 | Horzewski et al. | |
| 6,355,030 B1 | 3/2002 | Aldrich et al. | |
| 6,371,978 B1 | 4/2002 | Wilson | |
| 6,374,476 B1 | 4/2002 | Ponzi et al. | |
| 6,402,780 B2 | 6/2002 | Williamson, IV et al. | |
| 6,402,781 B1 | 6/2002 | Langberg et al. | |
| 6,408,214 B1 | 6/2002 | Williams et al. | |
| 6,419,696 B1 | 7/2002 | Ortiz et al. | |
| 6,461,366 B1 | 10/2002 | Seguin | |
| 6,482,224 B1 | 11/2002 | Michler et al. | |
| 6,488,689 B1 | 12/2002 | Kaplan et al. | |
| 6,493,575 B1 | 12/2002 | Kesten et al. | |
| 6,497,707 B1 * | 12/2002 | Bowman et al. | 606/75 |
| 6,500,167 B1 | 12/2002 | Webster, Jr. | |
| 6,517,553 B2 * | 2/2003 | Klein et al. | 606/144 |
| 6,537,198 B1 | 3/2003 | Vidlund et al. | |
| 6,537,314 B2 | 3/2003 | Langberg et al. | |
| 6,551,271 B2 | 4/2003 | Nguyen | |
| 6,554,794 B1 | 4/2003 | Mueller et al. | |
| 6,554,852 B1 * | 4/2003 | Oberlander | 606/232 |
| 6,585,718 B2 | 7/2003 | Hayzelden et al. | |
| 6,599,311 B1 | 7/2003 | Biggs et al. | |
| 6,605,086 B2 | 8/2003 | Hayzelden et al. | |
| 6,610,058 B2 | 8/2003 | Flores | |
| 6,619,291 B2 | 9/2003 | Hlavka et al. | |
| 6,626,899 B2 | 9/2003 | Houser et al. | |
| 6,626,930 B1 | 9/2003 | Allen et al. | |

| | | | |
|---|---|---|---|
| 6,629,534 B1 | 10/2003 | St. Goar et al. | |
| 6,638,286 B1 * | 10/2003 | Burbank et al. ............ 606/157 | |
| 6,648,903 B1 | 11/2003 | Pierson, III | |
| 6,656,221 B2 | 12/2003 | Taylor et al. | |
| 6,676,702 B2 | 1/2004 | Mathis | |
| 6,706,065 B2 | 3/2004 | Langberg et al. | |
| 6,709,442 B2 | 3/2004 | Miller et al. | |
| 6,709,456 B2 | 3/2004 | Langberg et al. | |
| 6,712,804 B2 | 3/2004 | Roue et al. | |
| 6,718,985 B2 | 4/2004 | Hlavka et al. | |
| 6,719,767 B1 | 4/2004 | Kimblad | |
| 6,723,038 B1 | 4/2004 | Schroeder et al. | |
| 6,733,500 B2 | 5/2004 | Kelley et al. | |
| 6,746,472 B2 * | 6/2004 | Frazier et al. ............... 606/232 | |
| 6,755,812 B2 | 6/2004 | Peterson et al. | |
| 6,761,734 B2 | 7/2004 | Suhr | |
| 6,764,510 B2 | 7/2004 | Vidlund et al. | |
| 6,770,070 B1 | 8/2004 | Balbierz | |
| 6,790,231 B2 | 9/2004 | Liddicoat et al. | |
| 6,800,090 B2 | 10/2004 | Alferness et al. | |
| 6,810,882 B2 | 11/2004 | Langberg | |
| 6,824,562 B2 | 11/2004 | Mathis et al. | |
| 6,852,124 B2 | 2/2005 | Cox et al. | |
| 6,890,353 B2 | 5/2005 | Cohn et al. | |
| 6,905,476 B2 | 6/2005 | Ponzi | |
| 6,908,478 B2 | 6/2005 | Alferness et al. | |
| 6,911,035 B1 | 6/2005 | Blomme | |
| 6,951,549 B1 | 10/2005 | Beyerlein | |
| 6,960,229 B2 | 11/2005 | Mathis et al. | |
| 6,964,683 B2 | 11/2005 | Kowalsky et al. | |
| 6,966,926 B2 | 11/2005 | Mathis | |
| 6,989,028 B2 | 1/2006 | Lashinski et al. | |
| 6,997,951 B2 | 2/2006 | Solem et al. | |
| 7,073,504 B2 | 7/2006 | Callister et al. | |
| 7,087,064 B1 * | 8/2006 | Hyde ......................... 606/142 | |
| 7,104,999 B2 * | 9/2006 | Overaker ................... 606/142 | |
| 7,160,318 B2 | 1/2007 | Greenberg et al. | |
| 7,186,264 B2 | 3/2007 | Liddicoat et al. | |
| 7,247,149 B2 | 7/2007 | Beyerlein | |
| 7,364,567 B2 | 4/2008 | Beyerlein | |
| 2001/0003986 A1 | 6/2001 | Cosgrove | |
| 2001/0005787 A1 | 6/2001 | Oz et al. | |
| 2001/0018611 A1 | 8/2001 | Solem et al. | |
| 2001/0027322 A1 * | 10/2001 | Bowman .................... 606/104 | |
| 2001/0044568 A1 | 11/2001 | Langberg et al. | |
| 2002/0010483 A1 | 1/2002 | Folmer et al. | |
| 2002/0010486 A1 | 1/2002 | Hirt | |
| 2002/0013571 A1 | 1/2002 | Goldfarb et al. | |
| 2002/0016628 A1 | 2/2002 | Langberg et al. | |
| 2002/0026216 A1 | 2/2002 | Grimes | |
| 2002/0035361 A1 | 3/2002 | Houser et al. | |
| 2002/0042651 A1 | 4/2002 | Liddicoat et al. | |
| 2002/0077647 A1 | 6/2002 | Snow et al. | |
| 2002/0087169 A1 | 7/2002 | Brock et al. | |
| 2002/0087173 A1 | 7/2002 | Alferness et al. | |
| 2002/0103492 A1 | 8/2002 | Kaplan et al. | |
| 2002/0103532 A1 | 8/2002 | Langberg et al. | |
| 2002/0103533 A1 | 8/2002 | Langberg et al. | |
| 2002/0111637 A1 | 8/2002 | Kaplan et al. | |
| 2002/0161330 A1 | 10/2002 | Nguyen | |
| 2002/0165484 A1 | 11/2002 | Bowe et al. | |
| 2002/0165533 A1 | 11/2002 | Flores | |
| 2002/0165534 A1 | 11/2002 | Hayzelden et al. | |
| 2002/0169502 A1 | 11/2002 | Mathis | |
| 2002/0169504 A1 | 11/2002 | Alferness et al. | |
| 2002/0183836 A1 | 12/2002 | Liddicoat et al. | |
| 2002/0183837 A1 | 12/2002 | Streeter et al. | |
| 2002/0183841 A1 | 12/2002 | Cohn et al. | |
| 2002/0188170 A1 | 12/2002 | Santamore et al. | |
| 2003/0050598 A1 | 3/2003 | Hayzelden et al. | |
| 2003/0069593 A1 | 4/2003 | Tremulis et al. | |
| 2003/0078465 A1 | 4/2003 | Pai et al. | |
| 2003/0083538 A1 | 5/2003 | Adams et al. | |
| 2003/0093071 A1 | 5/2003 | Hauck et al. | |
| 2003/0105520 A1 | 6/2003 | Alferness et al. | |
| 2003/0120340 A1 | 6/2003 | Liska et al. | |
| 2003/0120341 A1 | 6/2003 | Shennib et al. | |
| 2003/0130731 A1 | 7/2003 | Vidlund et al. | |
| 2003/0144697 A1 | 7/2003 | Mathis | |
| 2003/0144732 A1 | 7/2003 | Cosgrove et al. | |
| 2003/0167071 A1 | 9/2003 | Martin et al. | |
| 2003/0171776 A1 | 9/2003 | Adams et al. | |
| 2003/0212453 A1 | 11/2003 | Mathis et al. | |
| 2003/0216764 A1 | 11/2003 | Tu et al. | |
| 2004/0010231 A1 | 1/2004 | Leonhardt et al. | |
| 2004/0044350 A1 | 3/2004 | Martin et al. | |
| 2004/0044365 A1 | 3/2004 | Bachman | |
| 2004/0049207 A1 | 3/2004 | Goldfarb et al. | |
| 2004/0059351 A1 | 3/2004 | Eigler et al. | |
| 2004/0098092 A1 | 5/2004 | Butaric et al. | |
| 2004/0138683 A1 | 7/2004 | Shelton et al. | |
| 2004/0138744 A1 | 7/2004 | Lashinski et al. | |
| 2004/0148020 A1 | 7/2004 | Vidlund et al. | |
| 2004/0153147 A1 | 8/2004 | Mathis | |
| 2005/0045183 A1 | 3/2005 | Callister et al. | |
| 2005/0055089 A1 | 3/2005 | Macoviak et al. | |
| 2005/0085844 A1 | 4/2005 | Tremulis et al. | |
| 2005/0209633 A1 | 9/2005 | Callister et al. | |
| 2005/0267571 A1 | 12/2005 | Spence et al. | |
| 2005/0267573 A9 | 12/2005 | Macoviak et al. | |
| 2006/0041306 A1 | 2/2006 | Vidlund et al. | |
| 2006/0095025 A1 | 5/2006 | Levine et al. | |

FOREIGN PATENT DOCUMENTS

| | | | |
|---|---|---|---|
| EP | 0377269 A1 | 7/1990 | |
| WO | WO 98/29041 A1 | 7/1998 | |
| WO | WO 99/00059 | 1/1999 | |
| WO | WO 99/13777 | 3/1999 | |
| WO | WO 99/30647 A1 | 6/1999 | |
| WO | WO 99/44534 A1 | 9/1999 | |
| WO | WO 00/03759 | 1/2000 | |
| WO | WO 00/06026 A2 | 2/2000 | |
| WO | WO 00/06027 A2 | 2/2000 | |
| WO | WO 00/06028 A1 | 2/2000 | |
| WO | WO 00/16700 A1 | 3/2000 | |
| WO | WO 00/60995 | 10/2000 | |
| WO | WO 01/00111 A1 | 1/2001 | |
| WO | WO 01/00114 A1 | 1/2001 | |
| WO | WO 01/26557 A1 | 4/2001 | |
| WO | WO 01/28432 A1 | 4/2001 | |
| WO | WO 01/28455 A1 | 4/2001 | |
| WO | WO 01/49213 A2 | 7/2001 | |
| WO | WO 01/49213 A3 | 7/2001 | |
| WO | WO 01/54618 A1 | 8/2001 | |
| WO | WO 01/89440 A2 | 11/2001 | |
| WO | WO 02/00099 A2 | 1/2002 | |
| WO | WO 02/01999 A2 | 1/2002 | |
| WO | WO 02/34167 A2 | 5/2002 | |
| WO | WO 02/39925 A2 | 5/2002 | |
| WO | WO 02/053206 A2 | 7/2002 | |
| WO | WO 02/060352 A2 | 8/2002 | |
| WO | WO 02/062263 A2 | 8/2002 | |
| WO | WO 02/062270 A1 | 8/2002 | |
| WO | WO 02/062408 A2 | 8/2002 | |
| WO | WO-02/063533 | 8/2002 | |
| WO | WO-02/078576 | 10/2002 | |
| WO | WO 03/049619 A2 | 6/2003 | |
| WO | WO 03/073913 A2 | 9/2003 | |
| WO | WO 2004/012789 A2 | 2/2004 | |
| WO | WO 2004/014282 A2 | 2/2004 | |

OTHER PUBLICATIONS

Messas, et al., "Chordal Cutting: a New Therapeutic Approach for Ischmic Mitral Regurgitation," American Heart Association Inc., 2001, pp. 1958-1963.

PCT Invitation to Pay Additional fees for PCT International Appln. No. US03/36633, mailed May 19, 2004 (5 pages).

PCT Report for PCT International Patent Application PCT/US2004/031403, mailed Jun. 15, 2005. 5 pgs.

Advanced Cardiovascular Systems, Inc., PCT International Preliminary Report on Patentability and Written Opinion for PCT Appln No. US2004/031403, mailed Apr. 13, 2006 (8 pages).

Advanced Cardiovascular Systems, Inc., PCT International Search Report and Written Opinion of the International Searching Authority for PCT Appln No. US2004/031403, mailed May 18, 2005 (15 pages).

Advanced Cardiovascular Systems, Inc., PCT International Search Report for PCT Appln No. US2004/031403, mailed Feb. 15, 2005 (5 pages).

* cited by examiner

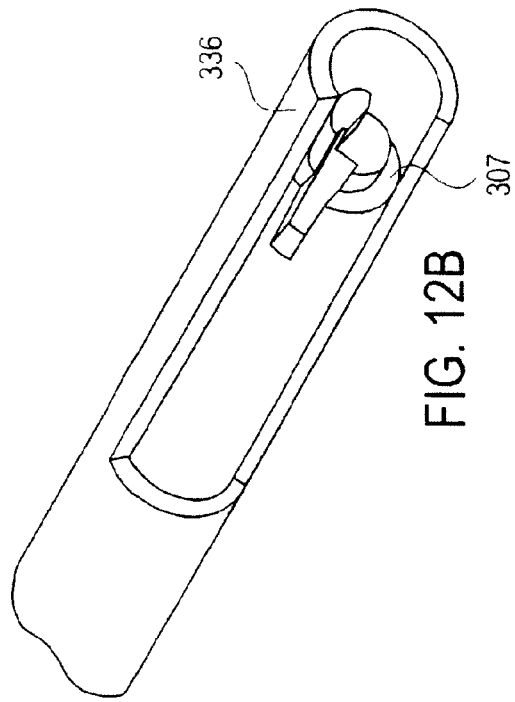
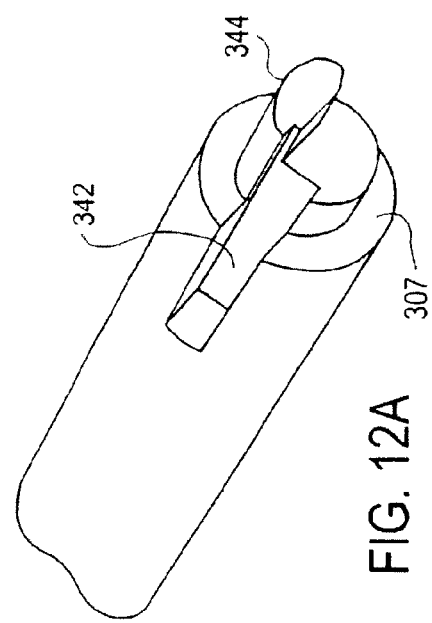
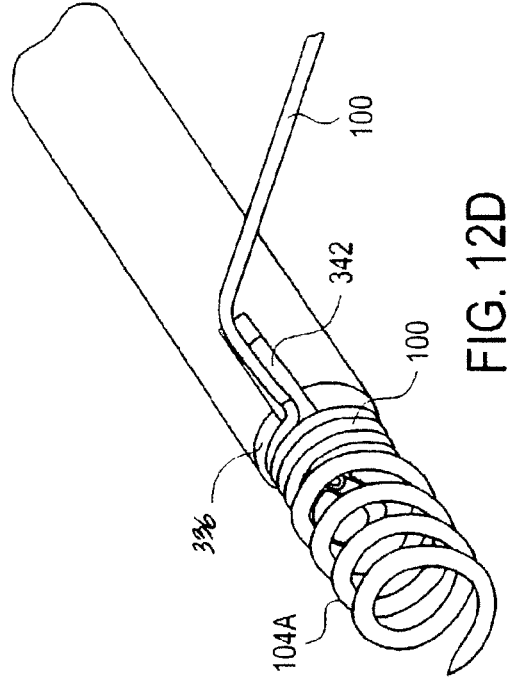
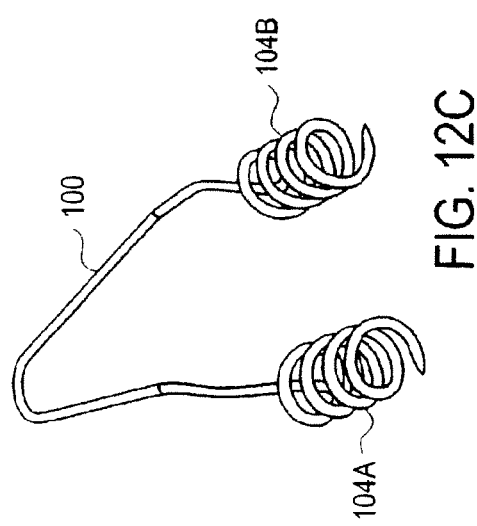
FIG. 12A
FIG. 12B
FIG. 12C
FIG. 12D

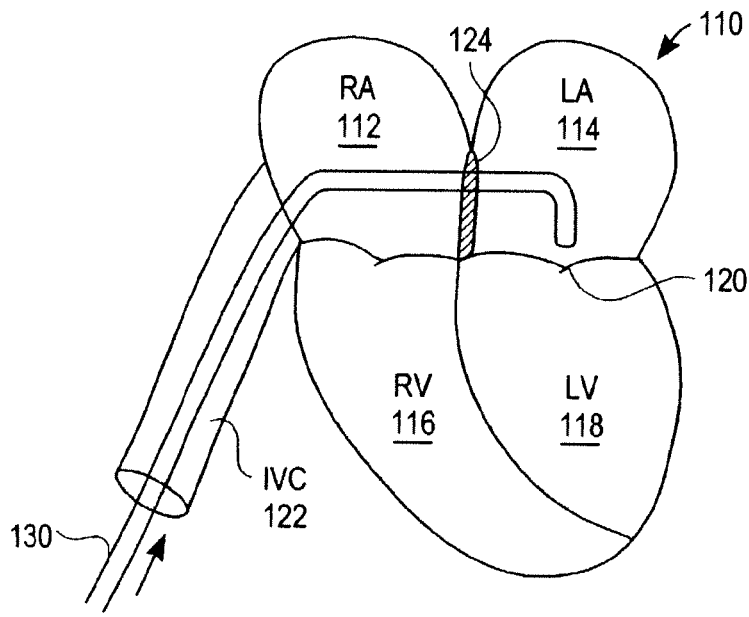
FIG. 14A
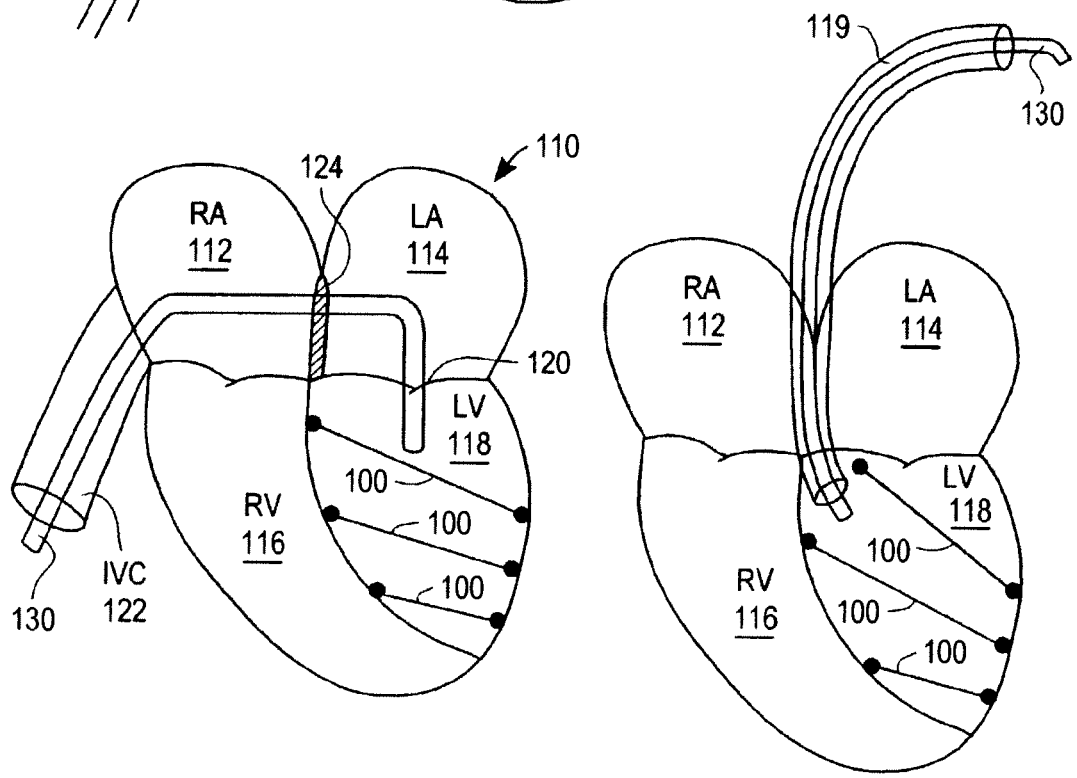
FIG. 14B
FIG. 14C

APPARATUSES AND METHODS FOR HEART VALVE REPAIR

CROSS-REFERENCE TO RELATED APPLICATIONS

This application is a continuation of co-pending U.S. patent application Ser. No. 11/240,589, filed Sep. 29, 2005, which is a divisional of U.S. patent application Ser. No. 10/272,060, filed Oct. 15, 2002, now U.S. Pat. No. 7,087,064.

BACKGROUND OF THE INVENTION

1. Field of the Invention

The present invention involves a medical device that is used for treating a defective heart valve.

2. Discussion of Related Art

FIG. 1A illustrates a heart 10. There are four valves in the heart 10 that serve to direct the flow of blood through the two sides of the heart 10 in a forward direction. The four valves are a mitral valve 20, an aortic valve 18, a tricuspid valve 60, and a pulmonary valve 62 as illustrated in FIG. 1A. The mitral valve 20 is located between the left atrium 12 and the left ventricle 14. The aortic valve 18 is located between the left ventricle 14 and the aorta 16. These two valves direct oxygenated blood coming from the lungs, through the left side of the heart, into the aorta 16 for distribution to the body. The tricuspid valve 60 is located between the right atrium 22 and the right ventricle 24. The pulmonary valve 62 is located between the right ventricle 24 and the pulmonary artery 26. These two valves direct de-oxygenated blood coming from the body, through the right side of the heart, into the pulmonary artery 26 for distribution to the lungs, where it again becomes re-oxygenated and distributed to the mitral valve 20 and the aortic valve 18.

All of the heart valves are complex structures. Each valve consists of moveable "leaflets" that are designed to open and close. The mitral valve has two leaflets and the tricuspid valve has three. The aortic and pulmonary valves have leaflets that are more aptly termed "cusps" and are shaped somewhat like a half-moon. The aortic and pulmonary valves each have three cusps.

Blood flows into the left ventricle 14 through the mitral valve 20 opens during diastole. Once the left ventricular cavity has filled, the left ventricle 14 contracts during systole. The mitral valve 20 closes (the leaflets of the mitral valve 20 re-approximate) while the aortic valve 18 opens during systole allowing the oxygenated blood to be ejected from the left ventricle 14 into the aorta 16. A normal mitral valve allows blood to flow into the left ventricle and does not allow leaking or regurgitating back into the left atrium and then into the lungs. The aortic valve allows blood to flow into the aorta and does not allow leaking (or regurgitating) back into the left ventricle. The tricuspid valve 60 functions similarly to the mitral valve to allow deoxygenated blood to flow into the right ventricle 24. The pulmonary valve 62 functions in the same manner as the aortic valve 18 in response to relaxation and contraction of the right ventricle 24 in moving de-oxygenated blood into the pulmonary artery and thence to the lungs for re-oxygenation.

With relaxation and expansion of the ventricles (diastole), the mitral and tricuspid valves open, while the aortic and pulmonary valves close. When the ventricles contract (systole), the mitral and tricuspid valves close and the aortic and pulmonary valves open. In this manner, blood is propelled through both sides of the heart.

The anatomy of the heart and the structure and terminology of heart valves are described and illustrated in detail in numerous reference works on anatomy and cardiac surgery, including standard texts such as Surgery of the Chest (Sabiston and Spencer, eds., Saunders Publ., Philadelphia) and Cardiac Surgery by Kirklin and Barrett-Boyes.

Regurgitation is a condition when leaflets of a heart valve do not completely close causing backflow of blood. For instance, in a condition typically called mitral valve prolapse, the leaflets of the mitral valve do not close properly and thus, there is backflow, or regurgitation, of blood into the left atrium and then into lungs. The heart then has to work harder to pump enough blood for the body, which can lead to heart damage. Regurgitation is common, and is occurring in about 7% of the population. Mitral valve regurgitation is caused by a number of conditions, including genetic defects, infections, coronary artery disease (CAD), myocardial infarction (MI) or congestive heart failure (CHF). Most cases are mild and if the symptoms are bothersome, they can usually be controlled with drugs.

In more serious cases, the faulty or defective valve can be repaired with a surgical procedure such as an annuloplasty. As illustrated in FIG. 1B, an annuloplasty 30 is a surgical procedure in which a synthetic ring 32 is placed around the valve rim (annulus) 34. Sutures 38 are put into the valve annulus 34 and the synthetic ring 32. This causes proper closing by shrinking the size of the valve opening 36. FIG. 1C illustrates another surgical procedure in which a heart valve such as the mitral valve 20 is repaired by reconstruction. First, at step A, a section P2 from the posterior leaflet 40 of the mitral valve 20 is excised. Then, sequentially at steps B, C, D, and E, sections P1 and P3 of the posterior leaflet 40 are sutured together. The reconstruction shrinks the size of the valve opening 36. In some instances, a faulty or defective valve must be surgically replaced with a new valve. Examples of new valves include homograft valves (valves harvested from human cadavers), artificial mitral valves, and mechanical valves.

All of the procedures above are typically major surgical procedures that require the opening of the chest by sternotomy or at best through small incisions in the chest wall, heart lung bypass and stopping the heart beat. These procedures are extremely invasive subjecting patients to a lot of pain and discomfort and these procedures require long recovery time and hospitalization time. In some instances, some patients may not tolerate surgery, for example, due to them having congestive heart failures. Thus, having alternative procedures as options to surgery is helpful.

SUMMARY OF THE INVENTION

The present invention discloses apparatuses and methods for treating a defective heart valve.

In one exemplary embodiment of the present invention, a medical device comprises a ligature, including a first anchoring member and a second anchoring member. The ligature is used to treat a heart having a faulty heart valve (e.g., a faulty mitral valve). The ligature is percutaneously deployable into a patient with a faulty heart valve, wherein the first anchoring member anchors to a first tissue area of the faulty heart valve and the second anchoring member anchors to a second tissue area of the faulty heart valve. The ligature constricts or reduces the size of the faulty heart valve.

In another exemplary embodiment of the present invention, a medical device comprises a delivery shaft having a delivery lumen, a proximal end, and a distal end. A first deployment shaft, extending from the proximal end to the distal end, is disposed within the delivery lumen. A second deployment shaft, extending from the proximal end to the distal end, is disposed within the delivery lumen. A ligature is releasably coupled to the delivery shaft. The ligature includes a first anchoring member and a second anchoring member. The delivery shaft deploys the ligature into a patient, wherein the first deployment shaft deploys the first anchoring member to a first tissue area of the patient, and the second deployment shaft deploys the second anchoring member to a second tissue area of the patient.

In another exemplary embodiment of the present invention, a method of constricting a heart valve of a patient comprises providing a medical device comprising a delivery shaft having a delivery lumen, a proximal end, and a distal end. The delivery shaft comprises a first deployment shaft and a second deployment shaft disposed within the delivery lumen. A ligature including a first anchoring member and a second anchoring member is releasably coupled to the delivery shaft wherein the first anchoring member is releasably coupled to the first deployment shaft and the second anchoring member is releasably coupled to the second deployment shaft. The method further comprises deploying the ligature into the patient wherein the first deployment shaft deploys the first anchoring member to a first tissue area around the heart valve, and the second deployment shaft deploys the second anchoring member to a second tissue area of the heart valve. Once deployed, the ligature anchors the first anchoring member to the first tissue area and the second anchoring member to the second tissue area.

In another exemplary embodiment of the present invention, a method of constricting a heart valve of a patient comprises providing a medical device comprising a delivery shaft having a delivery lumen, a proximal end, and a distal end. The delivery shaft comprises a first deployment shaft and a second deployment shaft disposed within the delivery lumen. The method further comprises coupling a first ligature to the delivery shaft and deploying the first ligature to a heart valve area of the patient and coupling a second ligature to the delivery shaft and deploying the second ligature to the heart valve area of the patient. Each of the ligatures includes a first anchoring member and a second anchoring member wherein the first anchoring member is releasably coupled to the first deployment shaft and the second anchoring member is releasably coupled to the second deployment shaft. The first deployment shaft deploys the first anchoring member to anchor the first anchoring member to the heart valve area to constrict the heart valve. The second deployment shaft deploys the second anchoring member to anchor the second anchoring member to the heart valve area to constrict the heart valve.

BRIEF DESCRIPTION OF THE DRAWINGS

The present invention is illustrated by way of example and not limitation in the figures of the accompanying drawings, in which like references indicate similar elements and in which:

FIG. 12A is an illustration of an exemplary embodiment of a deployment shaft that can be used to deploy a ligature made in accordance with the present invention;

FIG. 12B is an illustration of an exemplary embodiment of the deployment shaft shown in FIG. 12A being disposed within a deployment lumen of a delivery device;

FIG. 12C is an illustration of an exemplary embodiment of a ligature with helix ends as anchoring members made in accordance with the present invention;

FIG. 12D is an illustration of an exemplary embodiment of the ligature shown in FIG. 12C being disposed within the deployment shaft shown in FIG. 12B;

FIG. 14A is an illustration of an exemplary embodiment where a medical device made in accordance with the present invention can be inserted percutaneously into a patient to deploy a ligature to a heart valve area;

FIG. 14B is an illustration of another exemplary embodiment where a medical device made in accordance with the present invention can be inserted percutaneously into a patient to deploy a ligature to a heart valve area;

FIG. 14C is an illustration of an exemplary embodiment where a medical device made in accordance with the present invention can be inserted percutaneously into a patient to deploy a ligature to a ventricle area;

DETAILED DESCRIPTION OF THE PRESENT INVENTION

The present invention pertains to novel medical devices and methods of using these medical devices to treat defective or faulty heart valves. In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

Figure 1A:
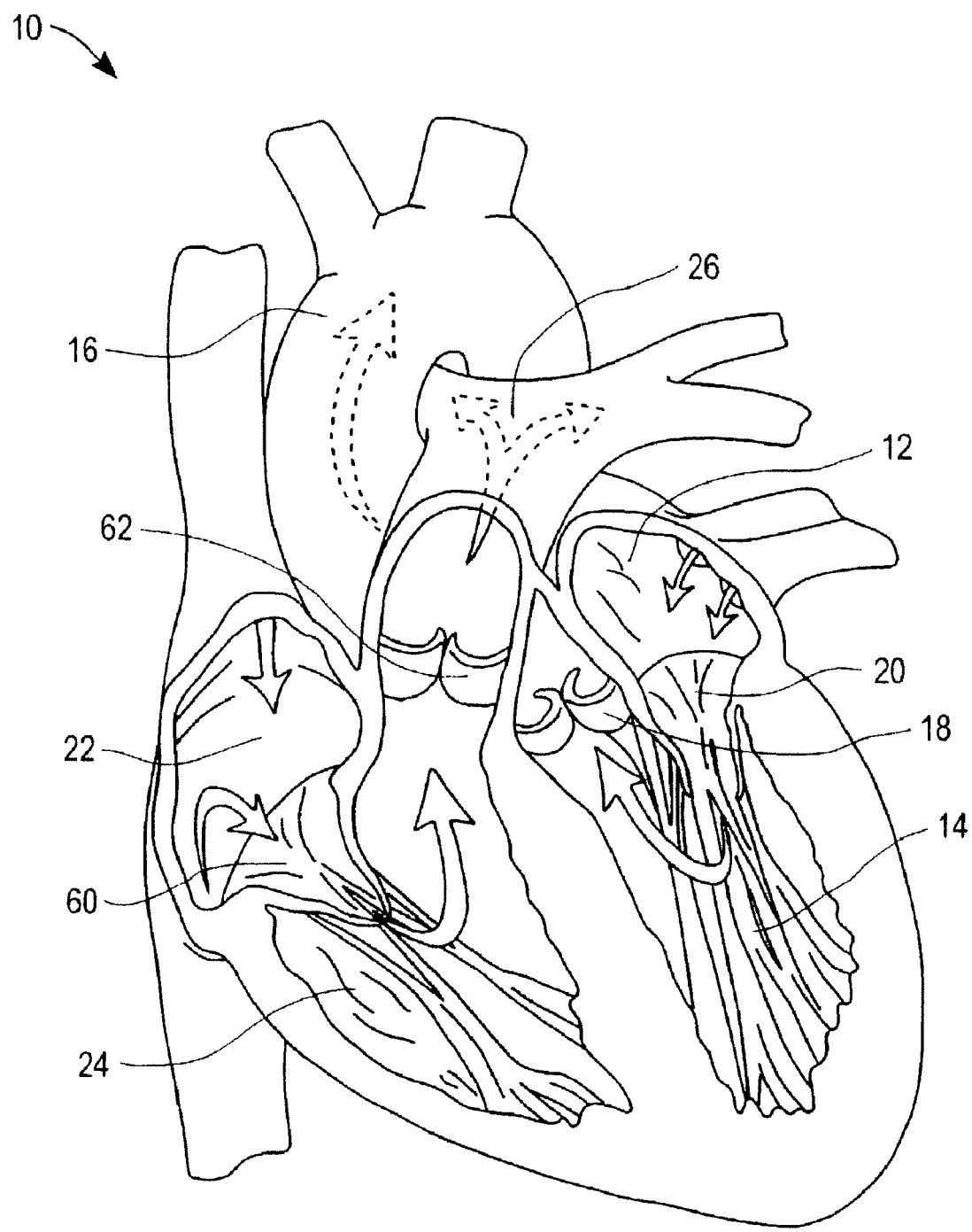
FIG. 1A is an illustration of a heart.
Figure 1B:
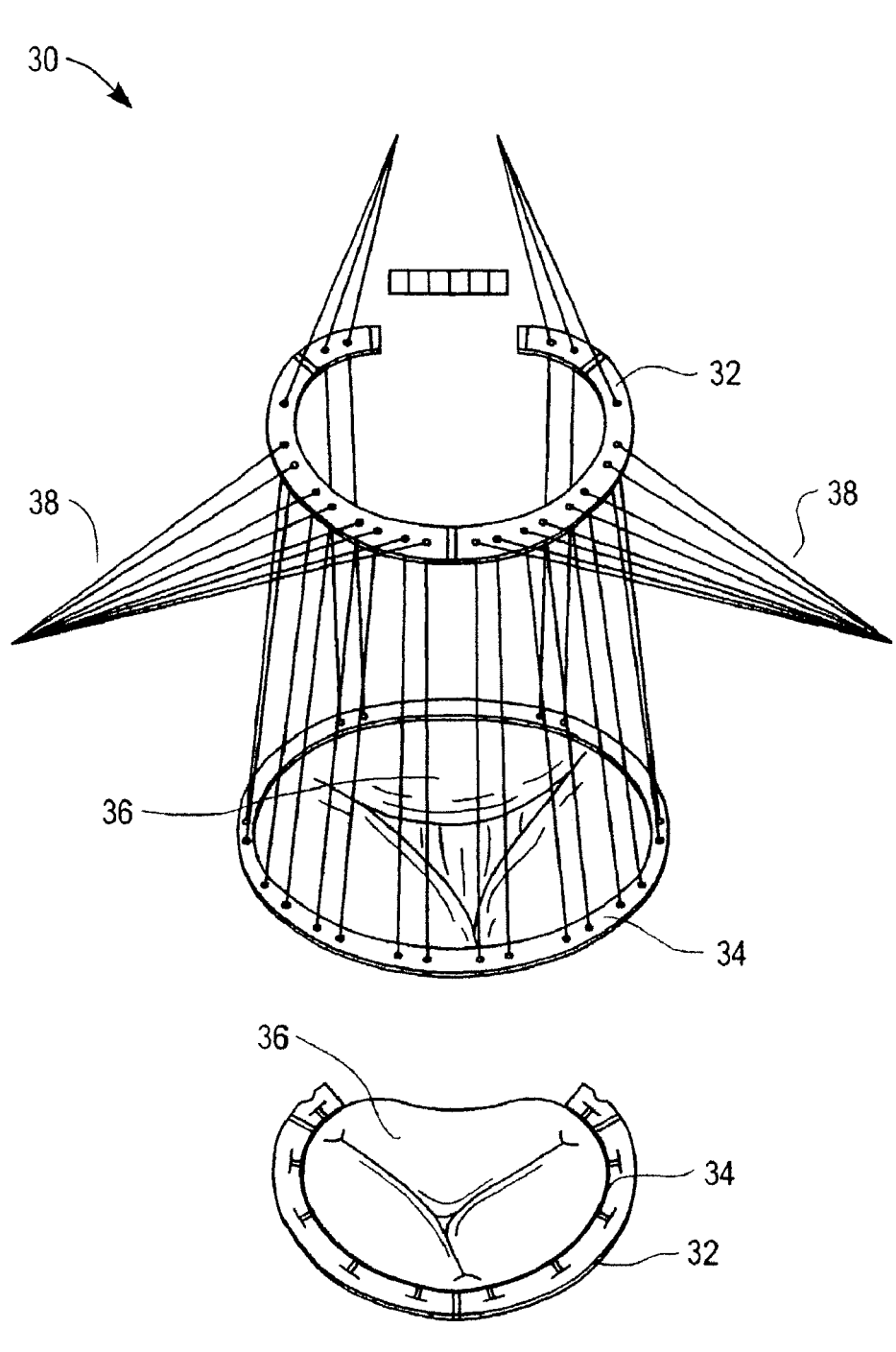
FIG. 1B is an illustration of an annuloplasty procedure to constrict a defective valve.
Figure 1C:
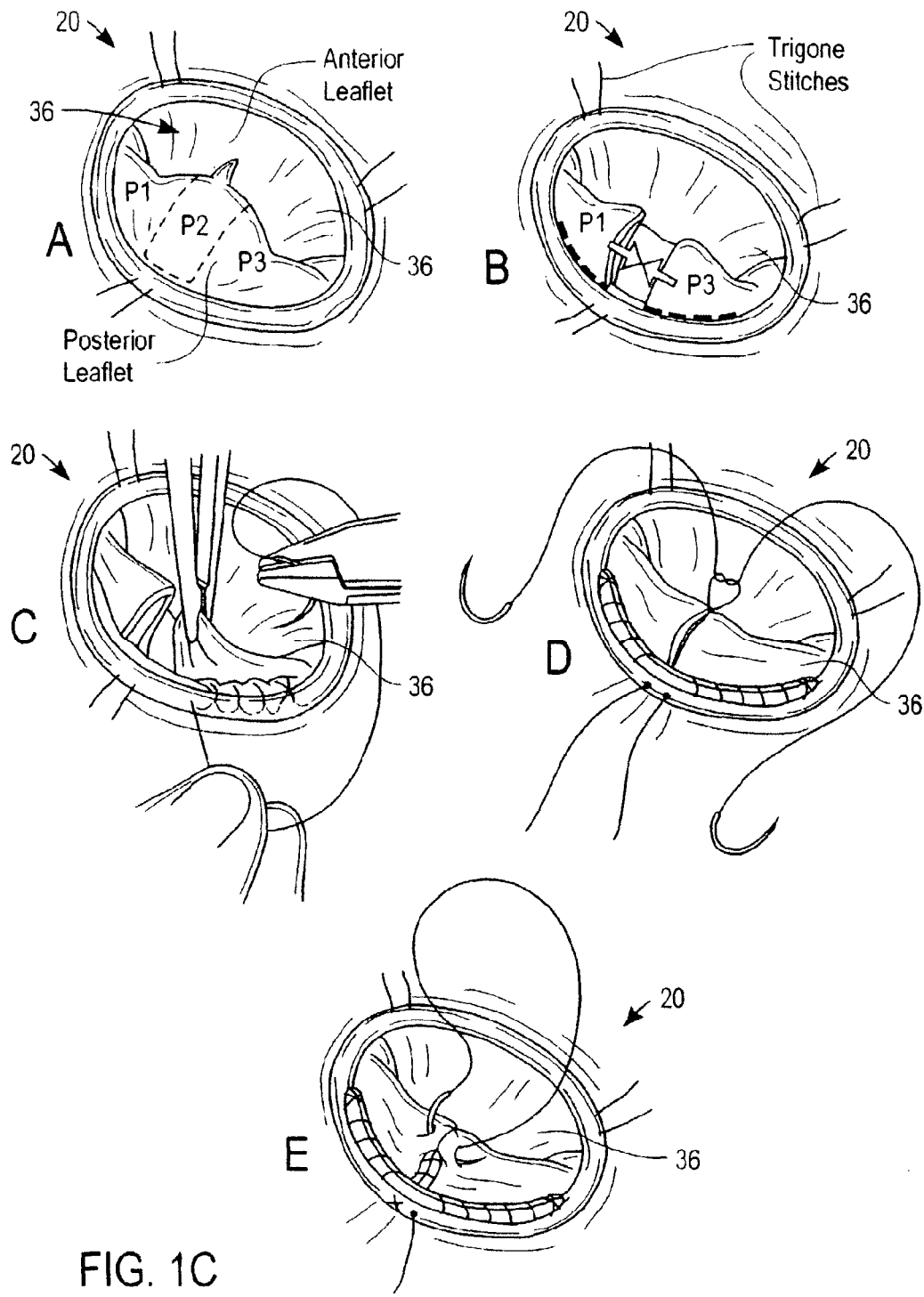
FIG. 1C is an illustration of a reconstruction procedure to reduce the size of a defective valve.
Figure 2A:
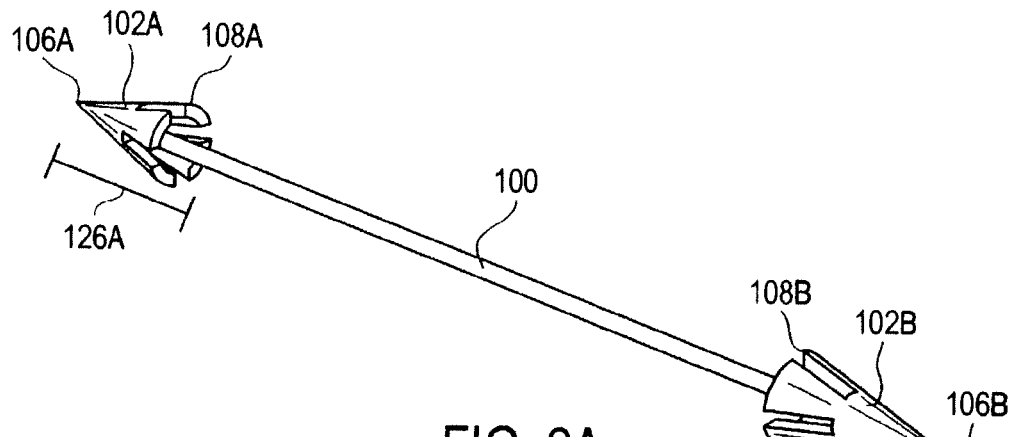
FIG. 2A is an illustration of an exemplary embodiment of a ligature in accordance with the present invention.

FIG. 2A illustrates an exemplary embodiment of a medical device that comprises a ligature 100. The ligature 100 can be a strap, string, cord, wire, bond, thread, suture, or other connector. The ligature 100 includes a first anchoring member 102A and a second anchoring member 102B. The ligature 100 serves to link together the first anchoring member 102A and the second anchoring member 102B. The ligature 100 can be percutaneously deployed into a patient with a faulty heart valve. By percutaneous deployment, the ligature 100 is deployed through blood vessels, veins, or arteries into a patient. In one embodiment, the ligature 100 is deployed through the blood vessels, veins, or arteries and into the heart area of a patient. The first anchoring member 102A and the second anchoring member 102B are then attached or anchored to a cardiac tissue (e.g., tissue around the heart valve). In one embodiment, the first anchoring member 102A and the second anchoring member 102B are not attached or anchored to a blood vessel, vein, or artery, and only attached or anchored to a cardiac tissue.

A faulty heart valve includes a heart valve that will not properly close causing backflow or regurgitation of blood. Such a faulty heart valve can be seen in a patient with a condition called regurgitation. In treating the faulty heart valve, the first anchoring member 102A anchors to a first tissue area of the faulty heart valve and the second anchoring member 102B anchors to a second tissue area of the faulty heart valve. The ligature 100 has a length that is sufficient to constrict or reduce the size of the heart valve once the anchoring members 102A and 102B are anchored into the tissue areas of the heart valve. Examples of a heart valve that can be treated with the ligature 100 include a mitral valve, an aortic valve, a tricuspid valve, and a pulmonary valve.

Although the ligature 100 is discussed in relation to treating a faulty heart valve, the ligature 100 may be used to treat other areas of a patient. For example, the ligature 100 can be used in ventricular remodeling to constrict, reshape, or reduce, the size of a left ventricle that has been enlarged due to some heart conditions. Alternatively, the ligature 100 can be used to close a vein or an artery of a patient.

The ligature 100 can be flexible or rigid. In one embodiment, the ligature 100 is made out of an elastic/resilient material, an elastomeric material, or a superelastic material. In one embodiment, the ligature 100 is made out of a superelastic nickel titanium, Nitinol, or stainless steel. In another embodiment, the ligature 100 is made out of a suture material suitable for suturing a tissue of a patient. The ligature 100 can be made out of existing suture materials such as polymers like PTFE, Polyethylene or similar polymers, and resorbable polymers. The ligature 100 can also be made out of an allograph material such as treated porcine, bovine or human tissue.

In one embodiment, a delivery device, described below, is used to deploy the ligature 100 to a heart to treat a faulty heart valve. Such a delivery device is able to attach the two anchoring members 102A and 102B of the ligature 100 to two different attachment sites (e.g., cardiac tissues or tissue areas within or proximate the heart). The anchoring member 102A is attached to one attachment site and the anchoring member 102B is attached to the other attachment site. During the attachment step, the ligature 100 may be stretched so as to reach both attachment sites. In some cases, the ligature 100 does not need to be stretchable for the anchoring members 102A and 102B of the ligature 100 to anchor into the two different attachment sites. After the attachment step, the ligature 100 is able to constrict or reduce the size of the heart valve. In the embodiment where the ligature 100 is flexible, the ligature 100 is stretched during the attachment step and is returned to its unstretched length after the attachment step thus, constricting (or reducing) the size of the heart valve. In the embodiment where the ligature 100 is rigid, the length of the ligature 100 is smaller than the size or the diameter of the heart valve thus, after the attachment step, the valve can be constricted or reduced.

In one embodiment, multiple ligatures 100 are placed across the faulty heart valve annulus to reshape or reduce the circumference or perimeter of the heart valve annulus. The ligature 100 may have cross section size that is sufficiently small to not significantly impede the flow of blood (or other fluid) through the heart valve or produce thrombus. The ligature 100 may be of a dimension that is similar to surgical sutures known in the field. The ligature 100 may have a cross section size between 0.001 mm and 5.0 mm. The ligature 100 may have a length between 10 mm and 600 mm. The ligature 100 may have an unstretched length between 10 mm and 600 mm that can be stretched to an appropriate length for deployment purposes and that can be returned to the unstretched length after the deployment of the ligature 100.

In some cases, the ligatures 100 are placed across a faulty heart valve and left in place for a specific period of time to improve the heart valve function. In other cases, the ligatures 100 aid in positive remodeling of the left ventricle by constricting (or reducing) the size of the faulty heart valve annulus so as to relieve the left ventricle from working extra hard to pump blood out of the left ventricle to other areas of the body. After this remodeling/recovery time a removal system could be employed at a later date to excise the ligatures 100.

In one embodiment, the ligature 100 has two ends wherein the first anchoring member 102A is attached to one end of the ligature 100 and the second anchoring member 102B is attached to the other end of the ligature 100. The anchoring members 102A and 102B are elements that can enter a tissue of a patient body (e.g., a cardiac tissue) and be anchored and retained therein. FIG. 2A illustrates an exemplary configuration of the anchoring members 102A and 102B, which are referred to as "barbed end" configurations. The anchoring members 102A and 102B have pointy ends 106A and 106B. The anchoring members 102A and 102B may also have a plurality of prongs 108A and 108B. The pointy ends 106A and 106B allow the anchoring members 102A and 102B to easily pierce through a tissue wall to begin the anchoring process. The prongs 108A and 108B prevent the anchoring members 102A and 102B from being detached or released from the tissue thus anchoring the anchoring members 102A and 102B to the tissue wall. Each of the anchoring members 102A and 102B has a predetermined length 126A and length 126B, which is dependent upon on the tissue depth that the each of the anchoring members 102A and 102B needs to pierce through to be anchored to the tissue.

Figure 2B:
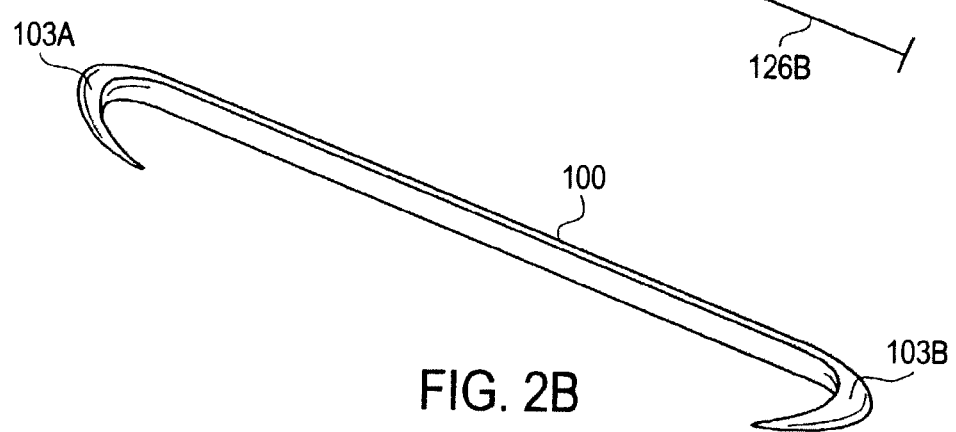
FIG. 2B is an illustration of another exemplary embodiment of a ligature in accordance with the present invention.

The anchoring members of the ligature 100 need not have the configurations shown in FIG. 2A. Another possible configurations includes a hook-end configuration as shown in FIG. 2B. The ligature 100 shown in FIG. 2B includes a first hook-end anchoring member 103A and a second hook-end anchoring member 103B. The first hook-end anchoring member 103A and the second hook-end anchoring member 103B can anchor the ends of the ligature 100 to a cardiac tissue similar to the anchoring members 102A and 102B shown in FIG. 2A.

Figure 3:
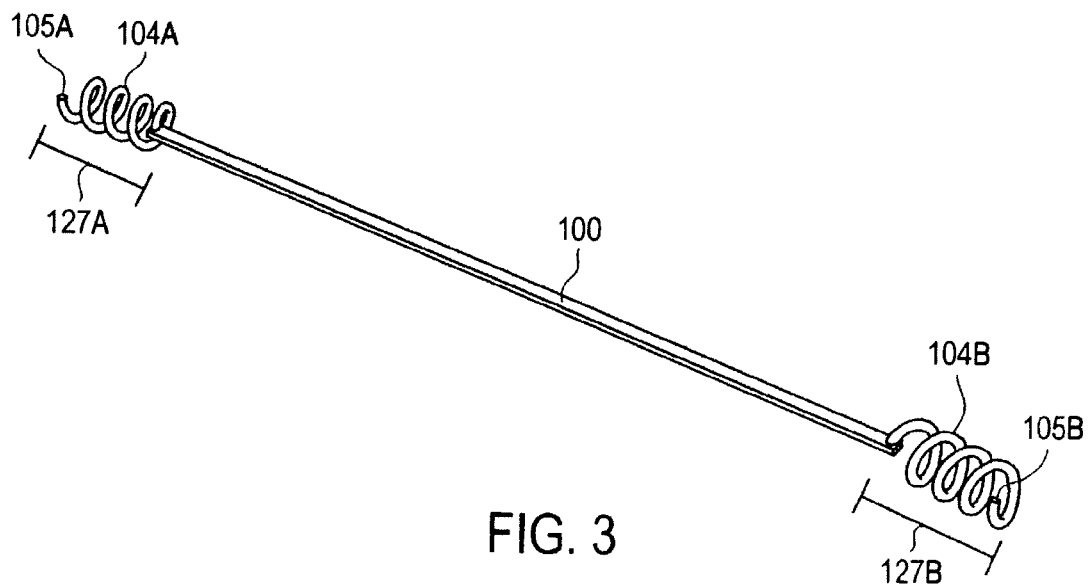
FIG. 3 is an illustration of another exemplary embodiment of a ligature in accordance with the present invention.

In one embodiment, the anchoring members have a helix end configuration as illustrated in FIG. 3. In this embodiment, the ligature 100 includes helix ends 104A and 104B. The helix ends 104A and 104B have ends 105A and 105B that may be pointy, sharp, or blunt depending on the type of tissue that the helix ends are to be anchored to. The helix ends 104A and 104B may be continuous helixes made of shape memory material that can maintains the helix ends 104A and 104B in their helical configuration. The helix ends 104A and 104B enter the tissue by threading and rotating through the tissue similar to action of a screw. Each of the anchoring members 104A and 104B has a predetermined length 127A and length 127B, which is dependent upon on the tissue depth that the each of the helix ends 104A and 104B needs to pierce through to be anchored to the tissue. In another embodiment, the ligature 100 includes double helix ends (not shown) to increase retentive or anchoring strength.

The anchoring members (e.g., the anchoring members 102A, 102B, 103A, 103B, 104A, and 104B) of the ligature 100 can be made out of metals, plastic, or any other hard materials that are biocompatible or implantable and are suitable for use in a patient's body. The anchoring members can also be made out of a semi stiff implantable material. The anchoring members can be made out of stainless steel, titanium, titanium alloy, nickel, nickel titanium alloy, chroma alloy or other suitable metal alloys. The anchoring members can also be made out of polymers, high density polyethylene (HDPE), polyglycolic acid, and polyglycolid hydroxyacetic acid. In one embodiment, the anchoring members or at least portions of the anchoring members are coated with a biocompatible lubricious material that provides for easier delivery and entrance into the tissue.

Figure 4:
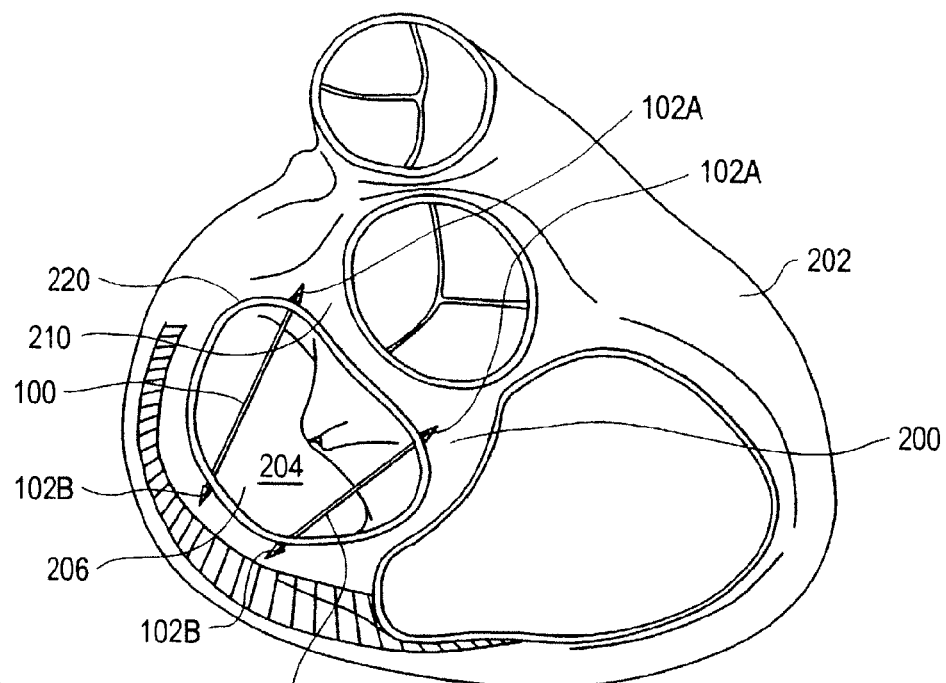
FIG. 4 is an illustration of an exemplary embodiment of two ligatures being placed across a mitral valve in a parallel pattern to constrict the mitral valve in accordance with the present invention.

FIG. 4 illustrates an exemplary embodiment where two of the ligatures 100 are placed across a heart valve such as a mitral valve. In FIG. 4, a heart 202 includes a mitral valve 204, a mitral valve annulus 206, a left fibrous ring 220, a right fibrous trigone 200 and a left fibrous trigone 210. The mitral valve 204 may be a faulty mitral valve such as those seen in patients having regurgitation. In one embodiment, the ligatures 100 (each including anchoring members 102A and 102B) are placed across the mitral valve 204 in a semi-parallel pattern. In one embodiment, an anchoring member 102A of a ligature 100 is placed in the left fibrous trigone 210 and an anchoring member 102B is placed in a location on the opposite side of the mitral valve annulus 206 in the left fibrous ring 220. Another anchoring member 102A of another ligature 100 is placed in the right fibrous trigone 200 and the other end of another ligature is placed in a location on the opposite side of the mitral valve annulus 206 in the left fibrous ring 220. If necessary, multiple ligatures 100 may be placed across the mitral valve annulus 206 in a semi-parallel pattern.

Figure 5:
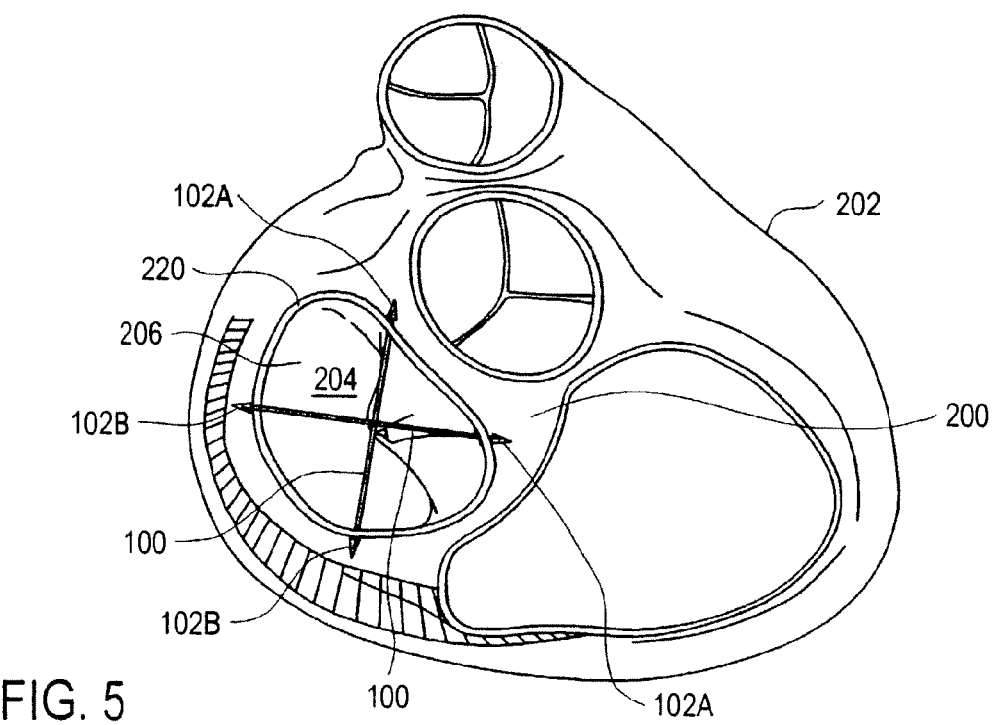
FIG. 5 is an illustration of another exemplary embodiment of two ligatures being placed across a mitral valve in an intersecting pattern to constrict the mitral valve in accordance with the present invention.

FIG. 5 illustrates another exemplary embodiment where two of the ligatures 100 are placed across a heart valve such as a mitral valve. The placement of the ligatures 100 in FIG. 5 is similar to the placement shown in FIG. 4 except that the ligatures 100 intersect or cross each other. In FIG. 5, a heart 202 includes a mitral valve 204, a mitral valve annulus 206, a left fibrous ring 220, a right fibrous trigone 200 and a left fibrous trigone 210. In one embodiment, the ligatures 100 (each including anchoring members 102A and 102B) are placed across the mitral valve 204 in an intersecting or cross pattern. In one embodiment, an anchoring member 102A of a ligature 100 is placed in the left fibrous trigone 210 and an anchoring member 102B is placed in a location on the opposite side of the mitral valve annulus 206 in the left fibrous ring 220. Another anchoring member 102A of another ligature 100 is placed in the right fibrous trigone 200 and the other end of this ligature 100 is placed in a location on the opposite side of the mitral valve annulus 206 in the left fibrous ring 220. If necessary, multiple ligatures 100 may be placed across the mitral valve annulus 206 in the intersecting or cross pattern.

It is to be appreciated that the semi parallel and the intersecting patterns can be combined together for the placements of the ligatures 100 if necessary. Additionally, the anchoring members of the ligatures shown in FIGS. 4 and 5 can have barbed end configurations as those shown for the anchoring members 102A or 102A, helix ends 104A or 104B, as those shown in FIG. 3 or hook ends 103A and 103B as those shown in FIG. 2B, or other types of ends that will anchor the ends of the ligature 100 to a tissue or a cardiac tissue. Also, a ligature 100 may include more than one anchoring member at each end of the ligature 100.

Figure 6:
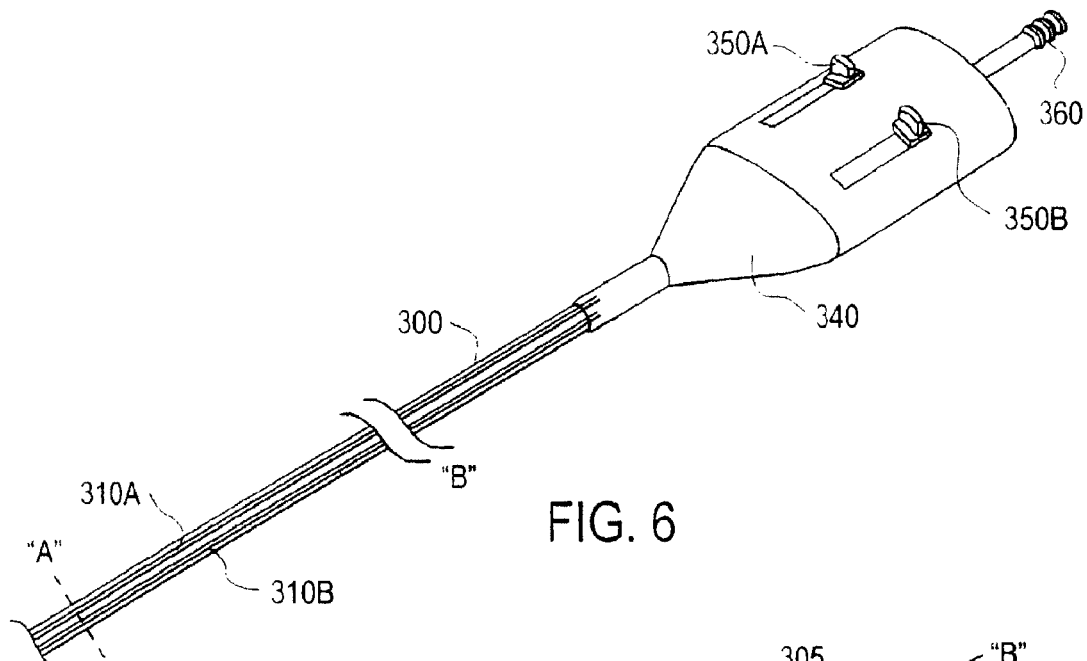
FIG. 6 is an illustration of an exemplary embodiment of a medical device that includes a delivery device which is used to percutaneously deploy a ligature into a patient to constrict a heart valve.
Figure 7:
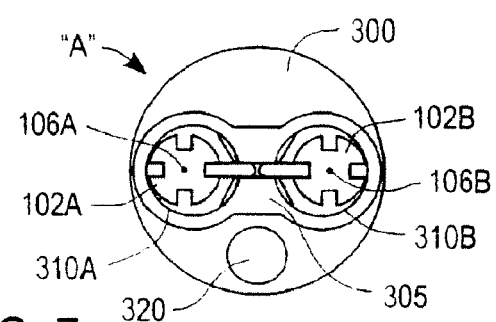
FIG. 7 is an illustration of a distal end of the medical device shown in FIG. 6 having a ligature disposed therein.
Figure 8:
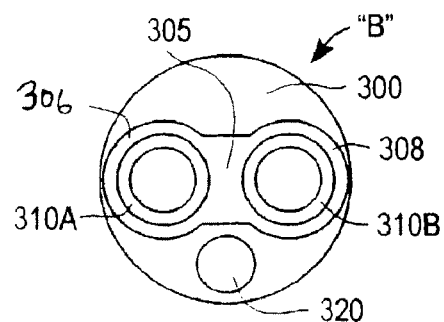
FIG. 8 is an illustration of a mid-section of the medical device shown in FIG. 6.

FIG. 6 illustrates a perspective view of one exemplary embodiment of a medical device 301 that includes a ligature 100 which can be used to percutaneously deploy a ligature 100 to a heart to treat a faulty heart valve. FIG. 7 illustrates a cross section "A" of the distal end 324 of the medical device 301. FIG. 8 illustrates a cross section "B" of the mid-section of the medical device 301.

In one embodiment, the medical device 301 comprises a delivery shaft 300 having a delivery lumen 305 (FIGS. 7-8), a proximal end 322, and a distal end 324. In one embodiment, the delivery shaft 300 is a catheter, which is sized and shaped as generally known in the art to travel within and along the vascular tree to the heart of a patient. A first deployment shaft 310A and a second deployment shaft 310B are disposed within the delivery lumen 305 and extend from the distal end 324 to the proximal end 322. A ligature 100 is releasably coupled to the delivery shaft 300 at the distal end 324 such that the ligature 100 is coupled to the delivery shaft 300 for deployment, and after deployment, the ligature 100 is released from the delivery shaft 300. The ligature 100 includes a first anchoring member 102A and a second anchoring member 102B and the ligature 100 links them as previously described. The medical device 301 can deploy the ligature 100 into a patient wherein the first deployment shaft 310A deploys the first anchoring member 102A to a first tissue area of the patient (e.g., a cardiac tissue, a tissue proximate a mitral valve, or a portion of the mitral valve) and the second deployment shaft 310B deploys the second anchoring member 102B to a second tissue area of the patient (e.g., another cardiac tissue, another tissue proximate a mitral valve, or another portion of the mitral valve).

In one embodiment, the ligature 100 is contained in the distal end 324 of the delivery shaft 300 near the cross section "A." The delivery lumen 305 may be a dumbbell shaped lumen 305. The dumb bell shaped lumen 305 provides a compartment in the distal end of the delivery shaft 300 where the ligature 100 can reside undisturbed as the medical device 301 is advanced to an area of the heart to be treated.

In one embodiment, the ligature 100 is housed inside the delivery lumen 305 on the distal end 324. The anchoring member 102A of the ligature 100 is mounted on the distal end of the deployment shaft 310A; and, the anchoring member 102B is mounted on the distal end of the deployment shaft 310B. In one embodiment, the deployment shaft 310A is housed in its own deployment lumen 306 and the deployment shaft 310B is housed in its own deployment lumen 308. The deployment lumens 306 and 308 may combine together to form the dumb bell shape lumen 305 or may be two separate lumens comprised within the delivery shaft 300. The delivery lumen 305 does not need to (but may) maintain its dumb bell shape for the entire length of the delivery shaft 300 or may only have the dumb bell shape at the distal end 324 of the delivery shaft 300. The delivery shaft 300 may include additional lumens such as additional lumens for the delivery of additional ligatures or for sensing endoscopy or to allow a pull wire to be used to deflect the distal end 324 (in order to control the positions where the anchoring members are anchored).

In one embodiment, the delivery shaft 300 is further coupled to a handle member 340, which is used in deploying the ligature or ligatures 100 as shown in FIG. 6. The handle member 340 includes a deployment mechanism 350A and a deployment mechanism 350B, which can advance or retract the deployment shafts 310A and 310B, respectively, to deploy the ligature 100. In one embodiment, the proximal end of the deployment shaft 310A is connected to the deployment mechanism 350A. The proximal end of the deployment shaft 310B is connected to the deployment mechanism 350B.

In one embodiment, the delivery shaft 300 also includes a guide wire lumen 320 as shown in FIGS. 7-8. The guide wire lumen 320 extends from the distal end 324 of the delivery shaft 300 to the proximal end 322 of the delivery shaft 300, through the handle member 340, and is connected to a guide wire port 360 in the proximal end of the handle member 340. The guide wire lumen 320 is sufficiently sized and shaped to allow for the insertion of a guide wire (not shown). The guide wire may be disposed through the guide wire lumen 320 to guide or maneuver the delivery shaft 300 from the entrance of the patient's body through the body of the patient to reach the area of the heart where the ligature 100 will be deployed, e.g., a mitral valve. In one embodiment, the guide wire port 360 is used to control the advancement, movement, or steering of the guide wire through the patient's body.

In one embodiment, the delivery shaft 300 may include reinforcement member such as a plurality of strands disposed in braided pattern, a plurality of fibers kitted together, or a coiled wire (not shown). In another embodiment, the delivery shaft 300 may comprise other lumens or supporting member (not shown) that can be used to steer or aim the distal end 324 of the medical device 301 in a desired direction. These supporting members may be of a pre-shaped nature curving the delivery shaft 300 as the supporting members are advanced within a lumen to the distal end 324 of the delivery shaft 300. One or more of these steering lumen and supporting member may be present in the delivery shaft 300.

In another embodiment, a supporting member may consist of a member (not shown) that is coupled to the distal end 324 of a steering lumen included within the delivery shaft 300. The steering lumen can be the guidewire lumen 320 shown in FIGS. 7-8. The supporting member may extend from the distal end 324 to the proximal end 322 of the delivery shaft 300. In one embodiment, pulling on this supporting member at the proximal end 322 causes the distal end 324 of the delivery shaft to become curved. In another embodiment, the steering lumen is pressurized causing the distal end 324 of the delivery system to bend in a desired direction.

In one embodiment, the guide wire lumen 320 may only be present in the distal end 322 of the delivery shaft 300 as in common rapid exchange catheter design known in the art. A common rapid exchange catheter is well known in the art. In another embodiment, the guide wire lumen 320 may absent from the delivery shaft 300 and may be replaced by one or more tendons to produce a bendable tip delivery shaft 300.

The delivery shaft 300 may be made out of numerous different types of materials. In one embodiment, the delivery shaft 300 is made out of materials that are suitable for inserting into a patient's body. For example, the delivery shaft 300 may be made out of materials suitable for making a catheter. The delivery shaft 300 may be made out of polyether block amid (PEBA), polyethylene (PE), polyproplylene (PP), polyvinylchloride (PVC), polytetrafluoroethylene (PTFE), or polyurethane, or other types of biocompatible material.

In one embodiment, the delivery shaft 300 comprises at least one radiopaque marker to aid the operator (e.g., a physician) in the monitoring, placing, or inserting of the delivery shaft 300 into a patient. The radiopaque marker can be a band of radiopaque material disposed proximate the distal end 324 of the delivery shaft 300. The radiopaque material aids the operator in determining the location of the distal end 324 of the delivery shaft 300. Examples of a radiopaque material include gold, platinum, tungsten, iron, silver, and thermoplastic material loaded with a radiopaque filler such as barium sulfate, bismuth subcarbonate, bismuth trioxide, bismuth oxychloride, tungsten power, and depleted uranium, etc. In another embodiment, the delivery shaft 300 comprises at least one Magnetic Resonance Imaging (MRI) marker to aid the operator in the monitoring, placing, or inserting of the delivery shaft 300 into a patient. An example of an MRI marker materials include platinum, tungsten, iridium, barium sulfate, plastic, or other particles suitable for a MRI process. Alternatively, the MRI marker can be an active component such as a small circuit that can generate a radio frequency (RF) that an MRI scanner can detect.

Figure 9:
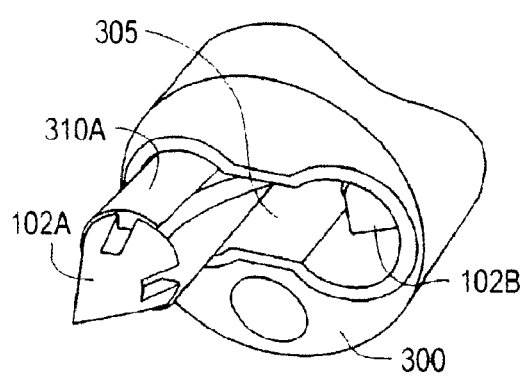
FIGS. 9-10 are illustrations of a perspective view of the medical device shown in FIG. 6 wherein a ligature is being deployed from the delivery shaft.

FIG. 9 illustrates a perspective view of the medical device 301 wherein the delivery shaft 300 is deploying the ligature 100 that is releasably coupled to the delivery shaft 300. In one embodiment, the medical device 301 is used to deploy the ligature 100 to place the ligature 100 across the mitral valve as illustrated in FIG. 4-5. The medical device 301 can be used to deploy the ligature 100 to other area of the heart, for example, within a coronary sinus (see FIG. 15A) or over the left ventricle of the heart (see FIGS. 14B and 14C).

Figure 10:
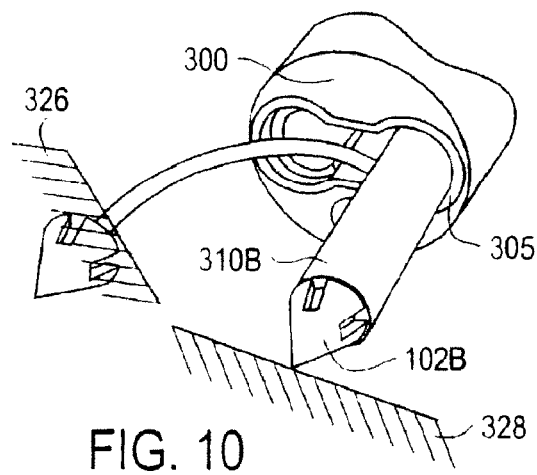

In one embodiment, advancing the deployment shaft 310A advances the anchoring member 102A of the ligature 100 out of the delivery shaft 300 as illustrated in FIG. 9. As the deployment shaft 310A is advanced, the anchoring member 102A is advanced from the lumen 305 at the distal end 324 of the delivery shaft 300 to a tissue area 326. Once the anchoring member 102A is anchored to the tissue area 326, the deployment shaft 310A can be retracted into the delivery shaft 300 leaving the anchoring member 102A embedded in the tissue area 326. In one embodiment, the deployment shaft 310A is retracted as illustrated in FIG. 10 wherein the anchoring member 102A is left attached or anchored to the tissue area 326. This process can be repeated for the anchoring member 102B of the ligature 100. The deployment shaft 310B is advanced out of the delivery shaft 300 thus advancing the anchoring member 102B. In one embodiment, the anchoring member 102B is anchored to a tissue area 328 which can be substantially opposite the tissue area 326 where the anchoring member 102A is anchored. Once the anchoring member 102B is anchored into the tissue area 328, the deployment shaft 310B is retracted into the delivery shaft 300.

In the embodiment where the ligature 100 is flexible, once both of the anchoring members 102A and 102B of the ligature 100 are anchored, the ligature 100 is allowed to return to its original length (unstretched length) or its original shape, thus, bringing the tissue areas 326 and 328 closer to each other. When the tissue areas 326 and 328 are brought closer to each other, the heart structure that the ligature 100 is placed across, e.g., the mitral valve, is narrowed, reduced, or constricted. In the embodiment where the ligature 100 is made of a rigid material, once the anchoring members 102A and 102B of the ligature 100 are anchored, the ligature 100 pull the tissue areas 326 and 328 are closer to each other. Again, when the tissue areas 326 and 328 are brought closer to each other, the heart structure that the ligature 100 is placed across, e.g., the mitral valve, is narrowed, reduced, or constricted.

The medical devices 301 shown in FIGS. 6-8 and 9-10 include the ligature 100 that has barbed end configurations for the anchoring members 102A and 102B. It is to be appreciated that the anchoring members 102A and 102B may have other configurations, for examples, helixes, or hooks as shown in FIGS. 2B and 3.

Figure 11A:
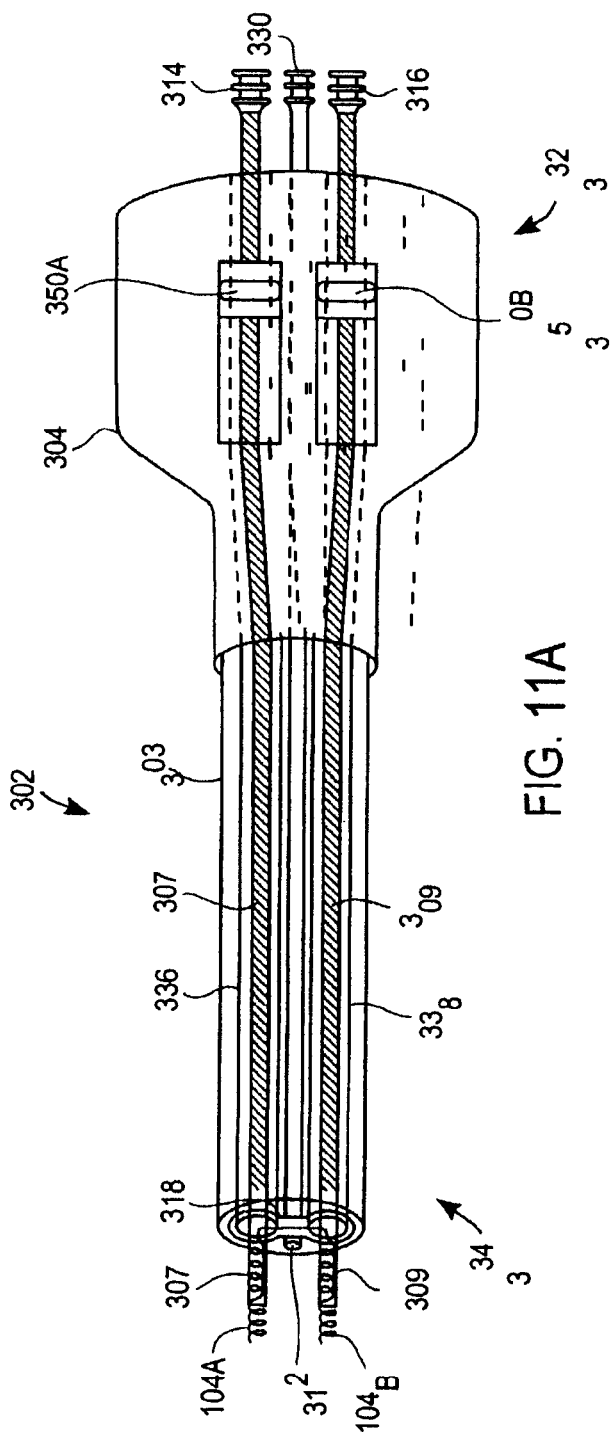
FIGS. 11A-11B illustrate another exemplary embodiment of a medical device that includes a delivery device which is used to percutaneously deploy a ligature into a patient to constrict a heart valve.
Figure 11B:
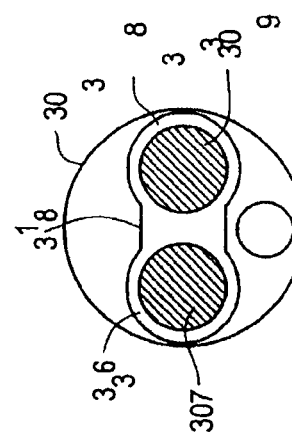

FIGS. 11A-11B illustrate an exemplary medical device 302. The medical device 302 is similar to the medical device 301 except that the device 302 is more preferred for delivering a ligature 100 that has helix ends as the anchoring members. As illustrated in FIGS. 11A-11B, the medical device 302 comprises a delivery shaft 303 having a delivery lumen 318, a proximal end 332, and a distal end 334. In one embodiment, the delivery shaft 303 is a catheter, which is sized and shaped as generally known in the art to travel within and along the vascular tree to the heart of a patient. In another embodiment, the delivery shaft 303 is the same as the delivery shaft 300.

In one embodiment, a first deployment shaft 307 and a second deployment shaft 309 are disposed within the delivery lumen 318 and extended from the distal end 334 to the proximal end 332. A ligature 100 is releasably coupled to the delivery shaft 303 at the distal end 334 such that the ligature 100 is coupled to the delivery shaft 303 for deployment, and after deployment, the ligature 100 is released from the delivery shaft 303. The ligature 100 includes a first anchoring member 104A and a second anchoring member 104B which are of helix ends. The medical device 302 can deploy the ligature 100 into a patient wherein the first deployment shaft 307 deploys the first anchoring member 104A to a first tissue area of the patient (e.g., a cardiac tissue, a tissue proximate a mitral valve, or a portion of the mitral valve) and the second deployment shaft 309 deploys the second anchoring member 104B to a second tissue area of the patient (e.g., a cardiac tissue, a tissue proximate a mitral valve, or a portion of the mitral valve).

In one embodiment, the ligature 100 is contained in the distal end 334 of the delivery shaft 303. The delivery lumen 318 may be a dumbbell shaped lumen 318. The dumb bell shaped lumen 318 provides a compartment in the distal end of the delivery shaft 303 where the ligature 100 can reside undisturbed as the medical device 302 is advanced through the patient's vasculature to an area of the heart to be treated.

In one embodiment, the ligature 100 is housed inside the delivery lumen 318 on the distal end 334. The anchoring member 104A of the ligature 100 is mounted on the distal end of the deployment shaft 307; and, the anchoring member 104B is mounted on the distal end of the deployment shaft 309. In one embodiment, the deployment shaft 307 is housed in its own deployment tube 336 and the deployment shaft 308 is housed in its own deployment tube 338 as illustrated in FIG. 11B. The deployment tubes 336 and 338 may combine together to form the dumb bell shape lumen 318 or may be two separate tubes disposed within the delivery shaft 303. The delivery lumen 318 does not need (but may) maintain its dumb bell shape for the entire length of the delivery shaft 303 or may only have the dumb bell shape at the distal end 334 of the delivery shaft 303.

In one embodiment, the delivery shaft 303 is further coupled to a handle member 304, which is used to deploy the ligature or ligatures 100. The handle member 304 includes a deployment mechanism 350A and a deployment mechanism 350B, which can advance or retract the deployment shafts 307 and 309, respectively, to bring the ligature 100 closer to the anchoring sites. In one embodiment, at least a section near the proximal end of the deployment shaft 307 is connected to the deployment mechanism 350A. A section near the proximal end of the deployment shaft 309 is connected to the deployment mechanism 350B. In one embodiment, as the deployment shafts 309 and 309 are advanced or retraced, the anchoring members 104A and 104B of the ligature 100 are advanced or retracted.

The handle member 304 also includes a rotating mechanism 314 and a rotating mechanism 316, which can rotate the deployment shafts 307 and 309 as the deployment shafts 307 and 309 are advanced or retracted. In one embodiment, the proximal end of the deployment shaft 307 is connected to the rotating mechanism 314. The proximal end of the deployment shaft 309 is connected to the rotating mechanism 316. In one embodiment, rotating the rotating mechanism 314 rotates the deployment shaft 307 thus rotating the anchoring member 104A. Similarly, rotating the rotating mechanism 316 rotates the deployment shaft 309 thus rotating the anchoring member 104B.

In one embodiment, the deployment tubes 336 and 338 are connected to the deployment mechanisms 350A and 350B, respectively. In this embodiment, the deployment tubes 336 and 338 are advanced or retracted by the deployment mechanisms 350A and 350B. As the deployment tube 336 and 338 are advanced or retracted, the deployment shafts 307 and 309 are also advanced or retracted. Thus, in this case, to deploy the anchoring members 104A and 104B, the deployment mechanisms 350A and 350B advance the deployment tubes 336 and 338, respectively. The deployment tubes 336 and 338 may be advanced completely out of the delivery shaft 303 or may only be partially advanced. Then, the deployment shafts 307 and 309 are then rotated by the rotating mechanisms 314 and 316, respectively to deploy the anchoring members 104A and 104B.

In one embodiment, the delivery shaft 303 also includes a guide wire lumen 312 as illustrated in FIGS. 11A-11B. The guide wire lumen 312 extends from the distal end 334 of the delivery shaft 303 to the proximal end 332 of the delivery shaft 303, and through the handle member 304 and is connected to a guide wire port 330 located at the proximal end of the handle member 304. The guide wire lumen is sufficiently sized and shaped to allow for the insertion of a guide wire (not shown). The guide wire may be disposed through the guide wire lumen 312 to guide or maneuver the delivery shaft 303 through the body of the patient to reach the area of the heart where the ligature 100 is to be deployed, e.g., a mitral valve. In one embodiment, the guide wire port is used to control the advancement, movement, or steering of the guide wire through the patient's body.

In one embodiment, the delivery shaft 303 may include reinforcement member similar to the delivery shaft 300 described above. In another embodiment, the delivery shaft 303 may comprise other lumens or supporting member that can be used to steer or aim the distal end 334 of the medical device 302 in a desired direction. These supporting members may be of a pre-shape nature curving the delivery shaft 303 as the supporting members are advanced within a lumen to the distal end 334 of the delivery shaft 303. One or more of these steering lumen and supporting member may be present in the delivery shaft 303.

In another embodiment, a supporting member may consist of a member (not shown) that is coupled to the distal end 334 of a steering lumen included within the delivery shaft 303. The steering lumen can be the guidewire lumen 312 shown in FIGS. 11A-11B. The supporting member may extend from the distal end 334 to the proximal end 332 of the delivery shaft 303. In one embodiment, pulling on this supporting member at the proximal end 332 causes the distal end 334 of the delivery shaft to become curved. In another embodiment, the steering lumen is pressurized causing the distal end of the delivery system to bend in a desired direction.

In one embodiment, the guide wire lumen 312 may only be present in the distal end 332 of the delivery shaft 303 as in common rapid exchange catheter design as is known in the art. In another embodiment, the guide wire lumen 312 may absent from the delivery shaft 303 and may be replaced by one or more tendons to produce a bendable tip delivery shaft 303.

The delivery shaft 303 may made out of numerous different types of materials similar to the material used to make the delivery shaft 300 described above. Also, similar to the delivery shaft 300, the delivery shaft 303 may also comprise at least one radiopaque marker or an MRI marker to aid the operator (e.g., a physician) in the monitoring, placing, or inserting of the delivery shaft 303 into a patient.

Figure 12F:
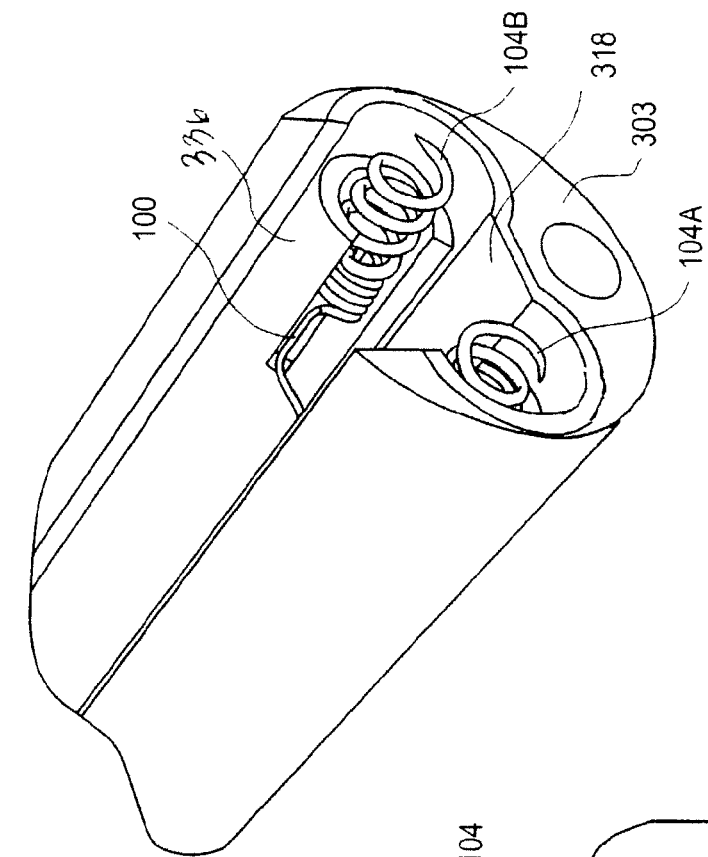
FIGS. 12F-12G are illustrations of a distal end of the medical device shown in FIG. 6 with a ligature having helix ends as anchoring members.

FIGS. 12A-12G illustrate an exemplary deployment shaft that can be used with the medical device 302 to deploy the ligature 100. The deployment shaft can be the deployment shaft 307 or 309 shown in FIGS. 11A-11B. In one embodiment, the deployment shaft 307 shown in FIG. 12A is disposed within the deployment tube 336 as shown in FIG. 12B. In one embodiment, the deployment shaft 307 includes a slot 342 wherein a portion of the ligature 100 can reside until deployment. The slot 342 is useful in that it helps keep the ligature 100 from being entangled between two deployment shafts 307 and 309. The slot 342 is not necessary for the deployment shaft 307 or 309 to function properly in deploying the ligature 100.

In one embodiment, a portion of the ligature 100 proximate the anchoring member 104A is spiraled around the deployment shaft 307 (as shown in FIG. 12D); and, the other portion of the ligature 100 proximate the anchoring member 104B would be spiraled around the deployment shaft 309 in a similar manner (not shown). In the embodiment where the deployment shafts 307 and 309 each includes a slot 342, the portion of the ligature 100 that is not wound around the deployment shafts 307 and 309 extends through the slot 342. The ligature 100 extending from one slot 342 of one deployment shaft (e.g., deployment shaft 307) can be inserted into another slot 342 on another deployment shaft (e.g., deployment shaft 309).

Figure 12E:
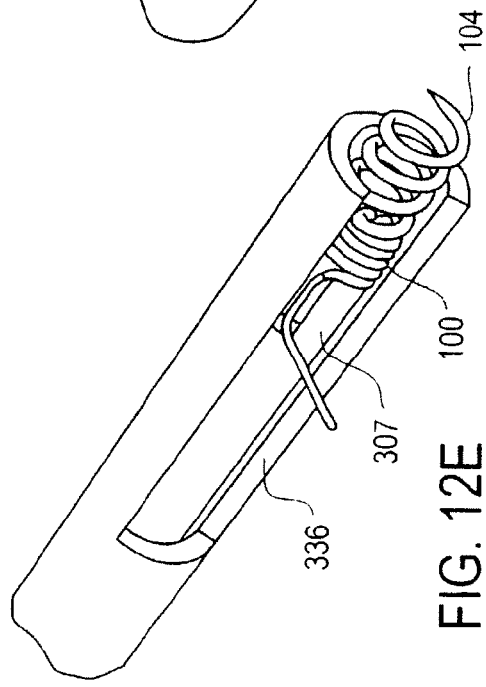
FIG. 12E is an illustration of an exemplary embodiment of the ligature shown in FIG. 12C being disposed within the deployment shaft shown in FIG. 12B which is disposed within a deployment lumen of a delivery device.
Figure 12G:
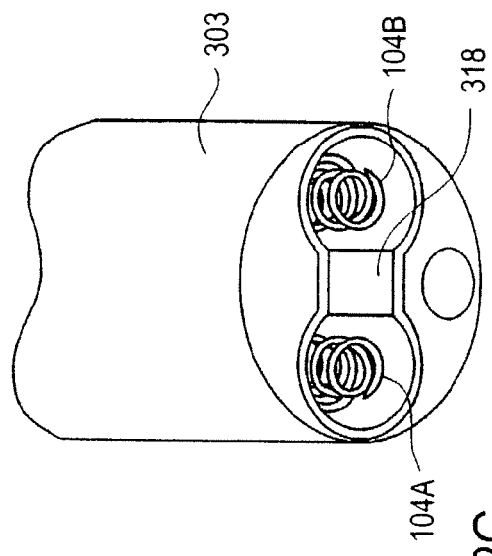

In one embodiment, the distal end of the deployment shaft 307 further comprises an axis 344 such that the helix anchoring member 104A can be kept there or releasably coupled thereto until the deployment of the ligature 100. The deployment shaft 307 with the ligature 100 releasably coupled thereto can be disposed within the deployment tube 336 as illustrated in FIG. 12E. FIGS. 12F-G further illustrates the distal end 334 of the delivery shaft 302 wherein the deployment shafts 307 and 309 are disposed within the deployment tube 336 and 338, respectively.

It is to be appreciated that a similar construction to the deployment shaft 307 can used for the ligature 100 with the barbed end configurations for the anchoring member 102A and 102B described above. In this embodiment, the barbed end will be kept at the axis 344 until after deployment.

Figure 13A:
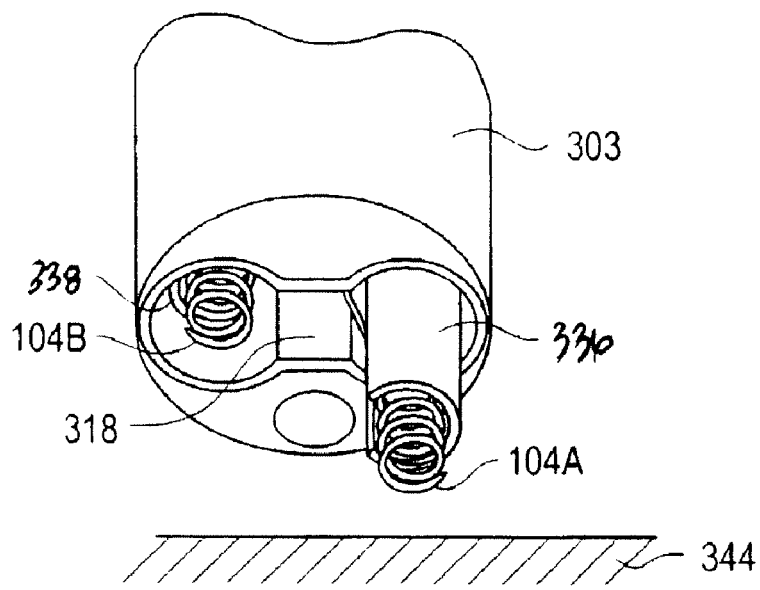
FIGS. 13A-13H are illustrations of an exemplary embodiment of a method to deploy a ligature or ligatures in accordance with the present invention.
Figure 13B:
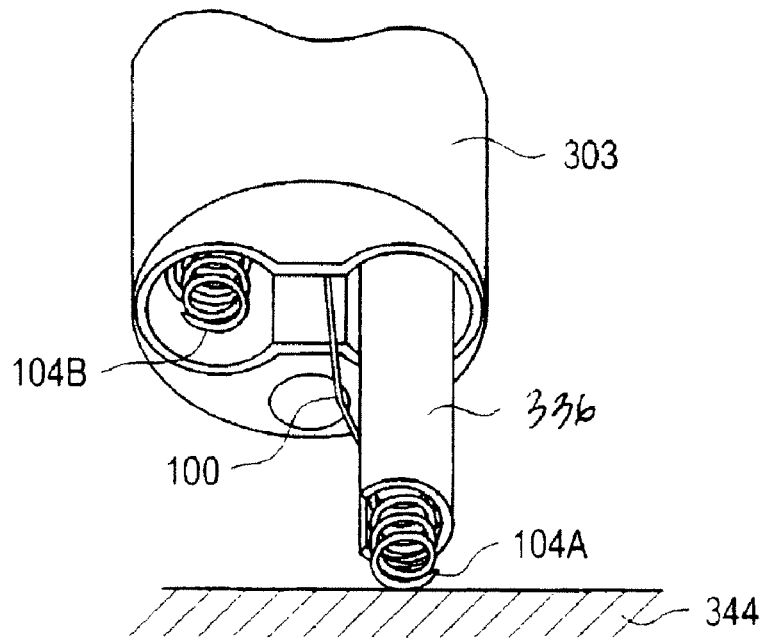
Figure 13C:
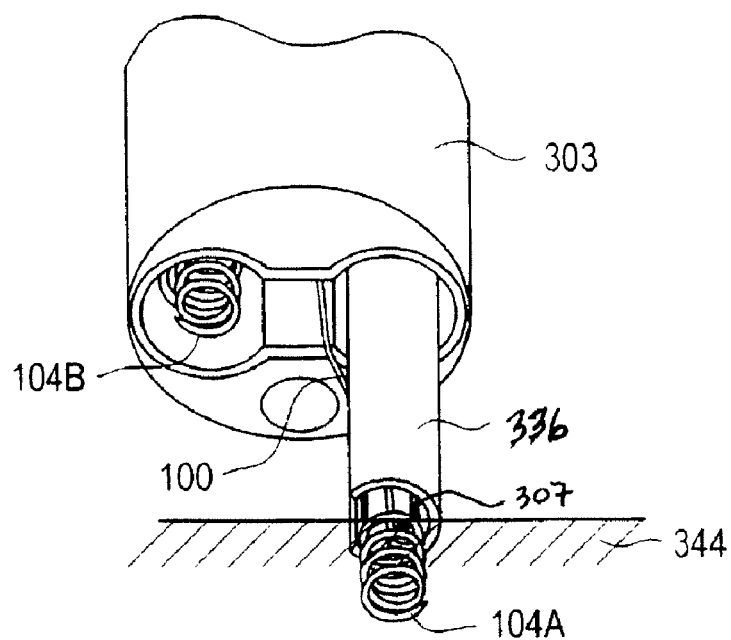
Figure 13D:
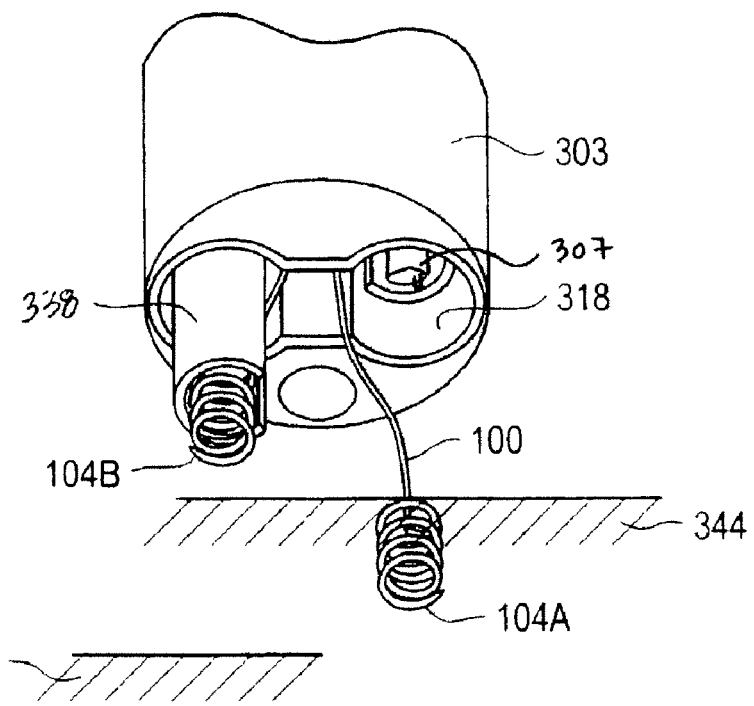

FIGS. 13A-13H illustrate an exemplary process of deploying the ligature 100 that includes helix ends anchoring members. At FIGS. 13A-13B, the deployment tube 336 is advanced in order to advance the deployment shaft 307 (not visible in these figures) toward a tissue area 344. Advancing the deployment shaft 307 would advance the helix ends 104A toward the tissue area 344. In one embodiment, the deployment tube 336 is advanced toward the tissue area 344 by a deployment mechanism, such as the deployment mechanism 350A shown in FIG. 11. After the advancement, the deployment shaft 307 is then rotated by a rotating mechanism such as the rotating mechanism 314 shown in FIG. 11. In this case, the linkage portion of the ligature 100 which joins the two anchoring members, the helix ends 104A and 104B, is flexible and twistable so that one helix end can be rotated while the other helix end is not. As the deployment shaft 307 is rotated, the helix end 104A is also rotated allowing it to pierce through the tissue area 344 as illustrated in FIG. 13C. In one embodiment, upon advancing, the helix end 104A is rotated in a direction that would enhance the advancement of the helix end 104A into the tissue area 344. The rotation of the deployment shaft 307 is initiated by a rotation of the rotating mechanism. Once the helix end 104A is anchored to the tissue area 344, the deployment tube 336 together with the shaft 307 is retracted into the delivery shaft 303 leaving the helix end 104A embedded (or anchored) in the tissue area 344 as illustrated in FIG. 13D. This process can be repeated for the helix end 104B of the ligature 100.

Figure 13E:
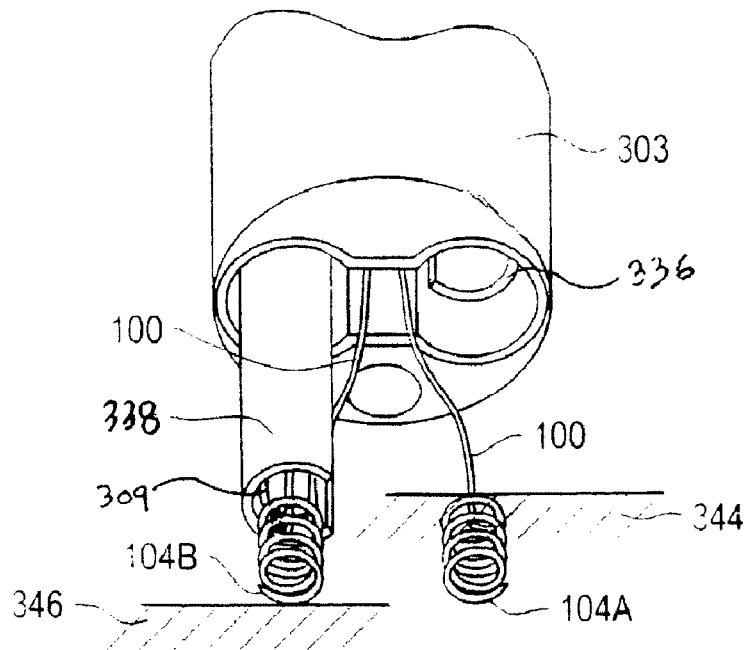
Figure 13F:
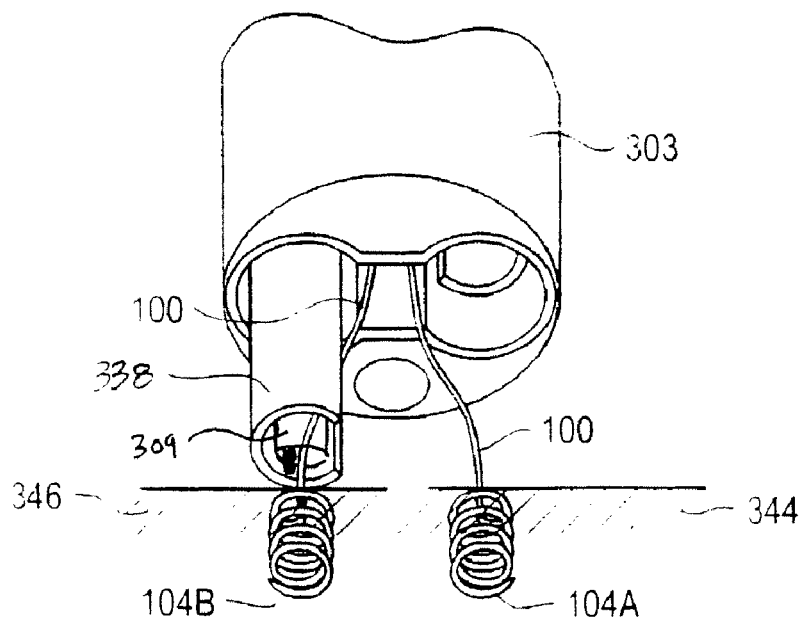
Figure 13G:
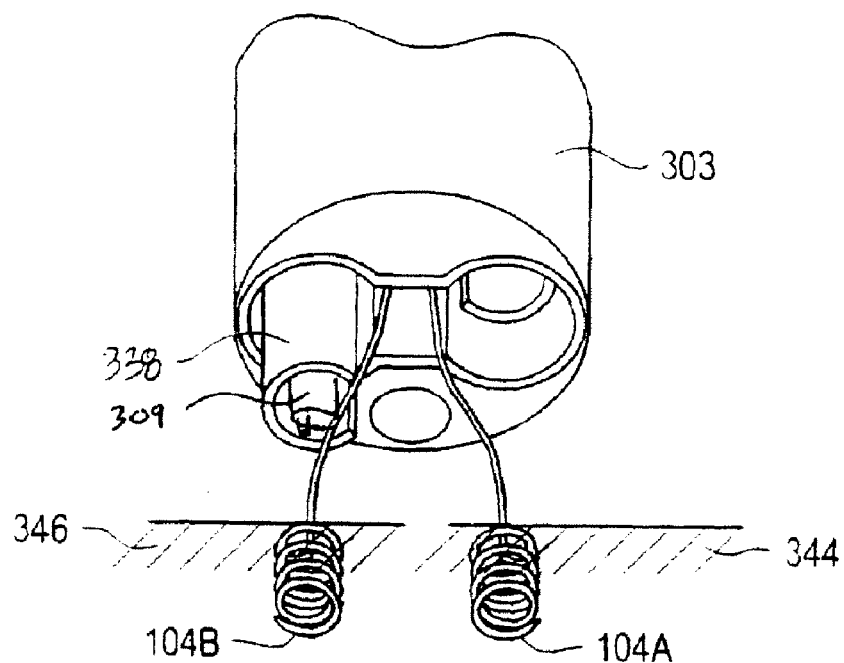
Figure 13H:
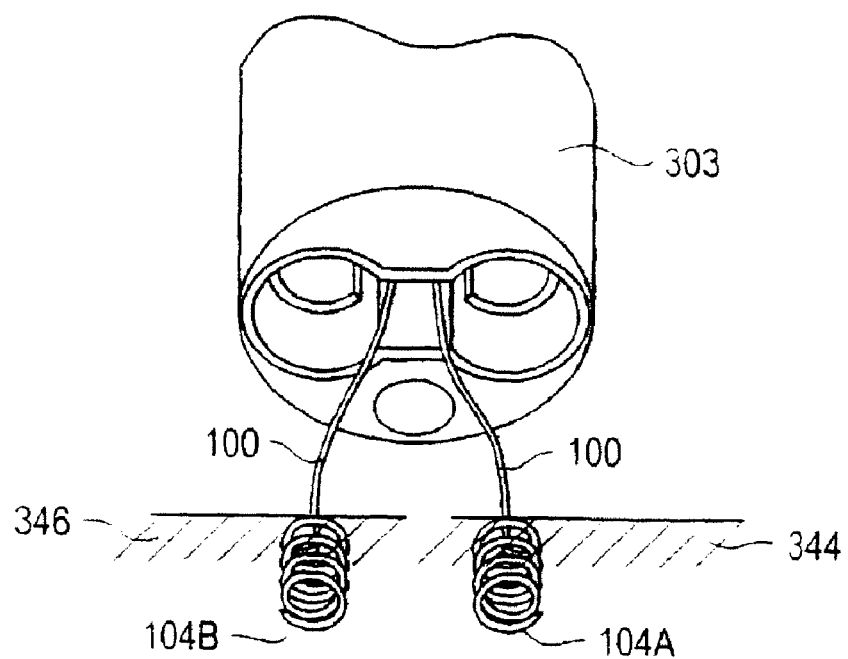

As shown in FIGS. 13D-13E, the deployment tube 338 is advanced out of the delivery shaft 303 to advance the deployment shaft 309 to a tissue area 346. Advancing the deployment shaft 309 would advance the helix end 104B toward the tissue area 346. After the advancement, the deployment shaft 309 is rotated by a rotating mechanism such as the rotating mechanism 316 shown in FIG. 11. As the deployment shaft 309 is rotated, the helix end 104B is also rotated allowing it to pierce through the tissue area 346 as illustrated in FIGS. 13E-F. In one embodiment, upon advancing, the helix end 104B is rotated in a direction that would enhance the advancement of the helix end 104B into the tissue area 346. Once the helix end 104B is anchored to the tissue area 346 as shown in FIG. 13F, the deployment shaft 309 is retracted into the delivery shaft 303 leaving the helix end 104B embedded in the tissue area 346 as illustrated in FIGS. 3G-H.

After the helix ends 104A and 104B are anchored to the tissue area 344 and 346, respectively, the delivery shaft 303 may then be retracted from the tissue area 344 and 346. The process described in FIGS. 13A-13H may be repeated as needed to deploy as many ligatures 100 as necessary. In one embodiment, the process is used to constrict a heart valve such as a mitral valve by placing multiple ligatures 100 across the mitral valve's annulus. In one embodiment, the tissue area 344 and 346 are the fibrous tissue around the annulus of the mitral valve. The anchoring of the helix ends 104A and 104B thus places the ligature 100 across the heart valve to reduce or constrict the size of the heart valve. The ligatures 100 with the helix ends can be placed across the mitral valve using this process to place the ligatures 100 similarly to what is depicted in FIGS. 4 and 5.

FIG. 14A illustrates an exemplary route of percutaneously inserting the ligatures 100 into a patient's heart 110. As previously mentioned, by percutaneous deployment, the ligature 100 is deployed through blood vessels, veins, or arteries into a patient. In one embodiment, the ligature 100 is deployed through the blood vessels, veins, or arteries and into the heart area of a patient.

In one embodiment, FIG. 14A illustrates an exemplary route of percutaneously inserting the ligatures 100 into the heart 110 and placing the ligatures 100 across the mitral valve 120 of the heart 110. In one embodiment, a medical device containing the ligature 100 is introduced into the patient's body percutaneously using a modified Seldinger technique in which the medical device is inserted into the venous vascular tree through the femoral vein. In one embodiment, the medical device enters or reaches the annulus of the mitral valve 120 from the atrial side of the heart 110. A medical device 130 is first provided. The medical device 130 can be the medial device 301 or the medical device 302 described above. The medical device 130 can also be a catheter capable of delivering and deploying a ligature 100 to the heart. The medical device 130 is advanced up the inferior vena cava (IVC) 122 and into the right atrium (RA) 112 of the heart 110. The medical device 130 then enters then left atrium (LA) 114 of the heart 110. In one embodiment, the medical device 130 crosses the atrial septum 124 through a small atrial septostomy (created by cardiological techniques known in the art) to enter the left atrium 114 of the heart 110. In one embodiment, a guidewire (not shown) is placed across the atrial septostomy and the medical device 130 is threaded along the guidewire and into the left atrium 114. The medical device 130 is stopped at a predetermined point in, at, or in proximity to the mitral valve 120. In one embodiment, the medical device 130 may have a preformed or deflectable short hook configuration at its tip region to facilitate the insertion of the medical device 130 into the mitral valve area. Once the medical device 130 reaches the area in, at, or in proximity to mitral valve 120, the ligature 100 can be deployed as previous described and be placed across the mitral valve in similar manners as those shown in FIGS. 4-5.

FIG. 14B illustrates an exemplary route of percutaneously inserting the ligatures 100 into a patient's heart 110 to perform a ventricular remodeling of the heart. In ventricular remodeling, the ligature (or ligatures) 100 can be used to reduce the size of the ventricle by placing these ligatures around the left ventricle (which is typically the ventricle that is enlarged due to a faulty mechanism in the heart such as regurgitation). With the ligatures 100 placed around the left ventricle, the size of the left ventricle can be reduced, hence, remodeled.

Continuing with FIG. 14B, in one embodiment, a medical device 130 is first provided. In one embodiment, the medical device 130 can be the medial device 301 or the medical device 302 described above. In another embodiment, the medical device 130 can be a catheter capable of delivering and deploying a ligature 100 to the heart. The medical device 130 is advanced up the inferior vena cava (IVC) 122 and into the right atrium (RA) 112 of the heart 110. The medical device 130 then enters then left atrium (LA) 114 of the heart 110. In one embodiment, the medical device 130 crosses the atrial septum 124 through a small atrial septostomy (created by cardiological techniques known in the art) to enter the left atrium 114 of the heart 110. In one embodiment, a guidewire (not shown) is placed across the atrial septostomy and the medical device 130 is threaded along the guidewire and into the left atrium 114. The medical device 130 is advanced through the mitral valve 120 to enter the left ventricle 118. In one embodiment, the medical device 130 may have a preformed or deflectable short hook configuration at its tip region to facilitate the insertion of the medical device 130 into the mitral valve area. Once the medical device 130 is inserted through the mitral valve 120, the ligature 100 can be deployed as previous described to anchor one of the anchoring members into the papillary muscles in the left ventricle 118 and the other anchoring member into a cardiac tissue opposite the heart muscles. This process is repeated to deploy several ligatures 100 as it may be necessary to employ more than one ligature to reduce the size of an enlarged left ventricle. In one embodiment, after several ligatures 100 have been deployed, the ligatures surround the left ventricle 118 as shown in FIG. 14B.

FIG. 14C illustrates another exemplary route of percutaneously inserting the ligatures 100 into a patient's heart 110 to perform a ventricular remodeling of the heart. A medical device 130 is first provided. In one embodiment, the medical device 130 can be the medial device 301 or the medical device 302 described above. In another embodiment, the medical device 130 can be a catheter capable of delivering and deploying a ligature 100 to the heart. The medical device 130 is advanced up the aorta 119 and directly into the left ventricle 118. In one embodiment, the medical device 130 may have a preformed or deflectable short hook configuration at its tip region to facilitate the insertion of the medical device 130 into the left ventricle 118. Once the medical device 130 reaches the left ventricle 118, the ligature 100 is deployed as previous described to place the ligature 100 into the tissues of the left ventricle 118. One such tissue is the heart muscles in the left ventricle 118. This process is repeated to deploy several ligatures 100 as it may be necessary to employ more than one ligature to reduce the size of an enlarged left ventricle. In one embodiment, after several ligatures 100 have been deployed, the ligatures span the interior of the left ventricle 118 as shown in FIG. 14C.

Figure 15A:
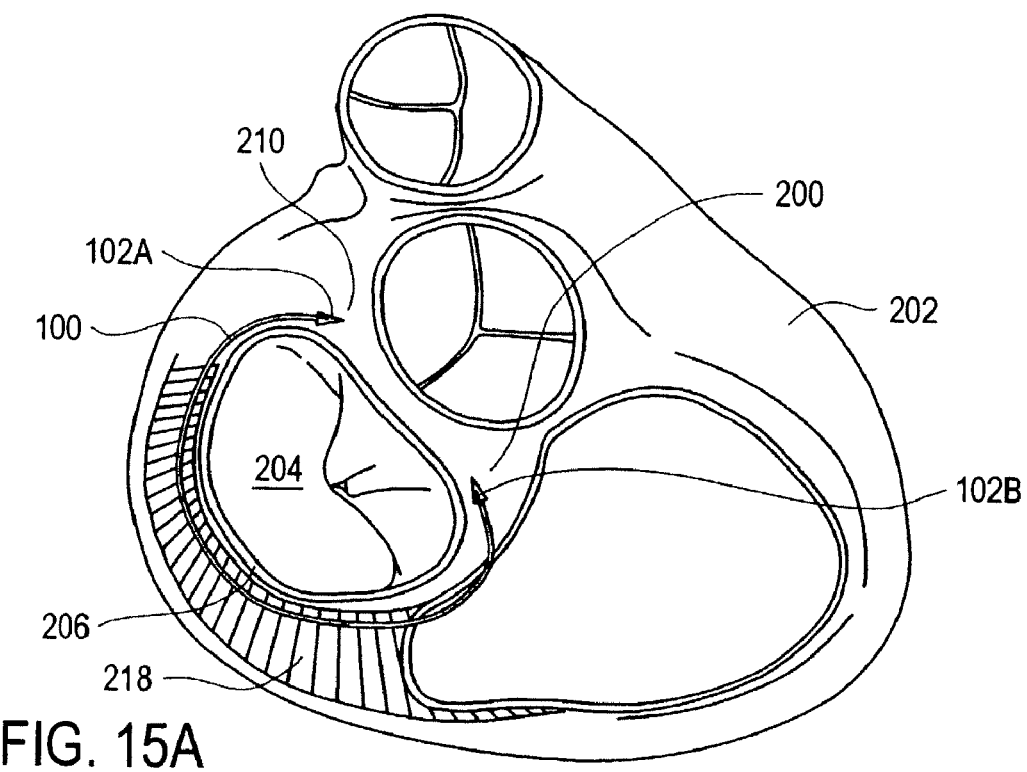
FIGS. 15A-15D are illustrations of an exemplary embodiment where a medical device made in accordance with the present invention can be inserted percutaneously into a coronary sinus.
Figure 15B:
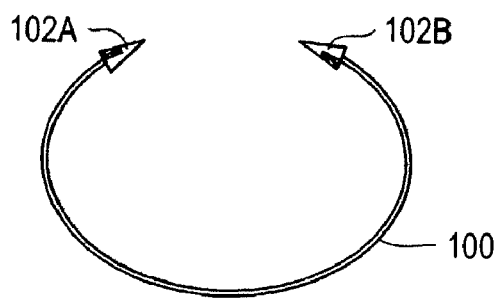
Figure 15C:
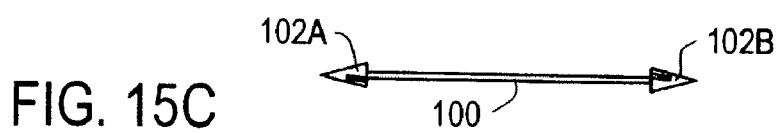
Figure 15D:
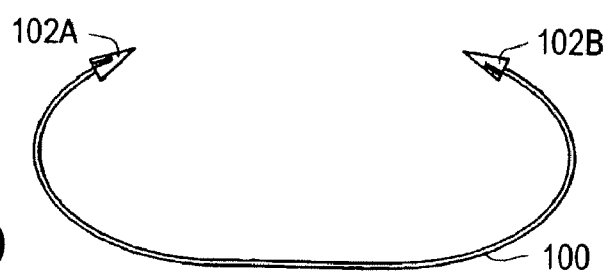

FIG. 15A illustrates an alternative embodiment of placing the ligature 100 around a mitral valve. In this embodiment, the ligature 100 described previously is placed within the coronary sinus 212 of the heart 202. The coronary sinus 212 substantially encircles the mitral valve annulus 206 of the mitral valve 204. A first anchoring member of the ligature 100 (e.g., the first anchoring member 102A) extends outside one end of the coronary sinus 218 and anchors into the left fibrous trigone 210. A second anchoring member of the ligature 100 (e.g., the second anchoring member 102B) extends outside the coronary sinus 218 and anchors into the right fibrous trigone 200. In one embodiment, the ligature 100 has a preformed shape such that once the ligature 100 is deployed and that the first and the second anchoring members are anchored, the ligature 100 bends and reduces the radius of curvature of the coronary sinus 218. In this embodiment, the ligature 100 can be made of a shape memory material and may be flexible or rigid. The ligature 100 may be made of a shape memory material such as Nitinol or other material that has a memory of an original shape as shown in FIG. 15B and can be temporarily stretched or forced into another shape during deployment as shown in FIG. 15C and FIG. 15D. Since the coronary sinus 218 substantially encircles the mitral valve annulus 206, the reduction of the radius of curvature of the bent coronary sinus 218 will result in a diameter and circumference reduction of the mitral valve annulus 206. In one embodiment the ligature 100 is surrounded or encapsulated by a jacket so as to prevent the ligature 100, once deployed within the coronary sinus 218, from cutting through the coronary sinus 218.

Figure 16:
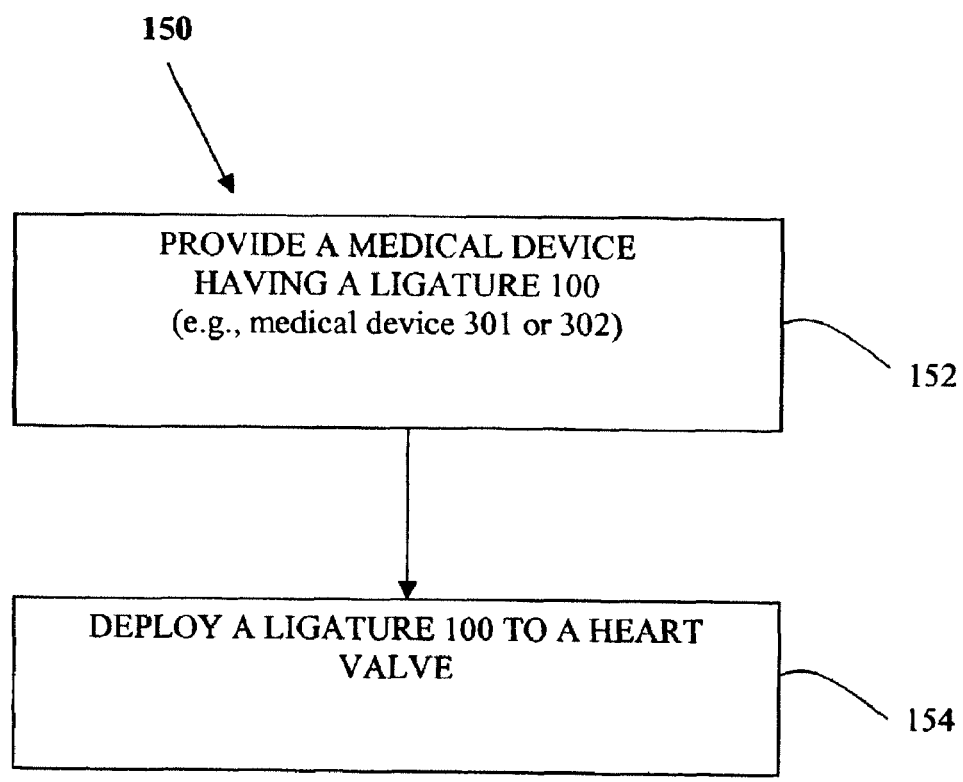
FIG. 16 is an illustration of an exemplary method of treating heart valve using medical devices made in according with the present invention.

FIG. 16 illustrates an exemplary method 150 of treating a faulty heart valve by constricting or reducing the size of the heart valve. At operation 152, a medical device such as the medical device 301 or 302 described above is provided. At operation 154, the ligature 100 is deployed into the patient wherein the first deployment shaft (e.g., the deployment shaft 310A, or 307) deploys the first anchoring member (e.g., the anchoring member 102A or 104A) to a first tissue area around the heart valve and the second deployment shaft (e.g., the deployment shaft 310B, or 309) deploys the second anchoring member (e.g., the anchoring member 102B or 104B) to a second tissue area of the heart valve. The ligature 100 can be deployed using the embodiments previously described. Deploying the ligature 100 anchors the first anchoring member to the first tissue area and the second anchoring member to the second tissue area as described above. The method 150 can be repeated in embodiments where multiple ligatures 100 are to be placed across the heart valve. The number of ligatures 100 sufficient to treat a faulty heart valve depends on how much of the size of the faulty heart valve needs to be constricted or reduced. The cross section size of each of the ligatures 100 is sufficiently small so as to not cause thrombus or to not significantly impede the blood flow through the heart valve. The length of each of the ligatures 100 can be varied depending on the area the ligature 100 needs to constrict or reduce.

The percutaneous methods described above can be used to place the ligature(s) 100 across the mitral valve to constrict (or reduce) the size of a faulty or defective heart valve. In one embodiment, the ligatures 100 are placed across the mitral valve in order to prevent back flow of blood that a patient with a regurgitation condition caused by a faulty mitral valve would experience. The described medical devices including the ligatures 100 that enable percutaneous introduction of the ligatures 100 into patients can replace those cases that require surgical procedures to reduce or constrict the mitral valve. Such a percutaneous method also reduces patient discomfort, improves recovery time, and reduces hospitalization time relatives to a surgical procedure in which the chest is opened.

I claim:

1. A medical device comprising:
    a first anchoring member to anchor to a cardiac tissue and a second anchoring member to anchor to the cardiac tissue;
    a ligature coupling the first anchoring member and the second anchoring member;
    a catheter having a size suitable for percutaneous insertion through a blood vessel and the catheter operable to be maneuvered through the blood vessel to the cardiac tissue, the catheter comprising a proximal end and a distal end and a lumen therethrough, the catheter configured to accommodate the ligature therein; and
    a delivery handle coupled to the proximal end of the catheter, wherein the delivery handle comprises a deployment mechanism to deploy the ligature from the catheter,
    wherein the delivery handle comprises a first deployment mechanism and a second deployment mechanism wherein the first deployment mechanism is configured for a dedicated deployment of the first anchoring member and the second deployment mechanism is configured for a dedicated deployment of the second anchoring member.

2. The medical device of claim 1, wherein the delivery handle further comprises a first rotating mechanism and a second rotating mechanism wherein the first rotating mechanism can rotate the first anchoring member accommodated at the distal end of the catheter and the second rotating mechanism can rotate the second anchoring member accommodated at the distal end of the catheter.

3. The medical device of claim 1, wherein the catheter further defines a dedicated guidewire lumen extending therethrough.

4. The medical device of claim 1, wherein the catheter further defines a first deployment lumen, a second deployment lumen, and a guidewire lumen.

5. The medical device of claim 4, further comprising a first deployment shaft coupled to the handle disposed in the first deployment lumen of the catheter and a second different deployment shaft coupled to the handle disposed in the second deployment lumen of the catheter.

6. The medical device of claim 1, wherein a lumen of the catheter may be pressurized to facilitate maneuvering of the catheter.

7. The medical device of claim 1, wherein the ligature comprises an elastic material.

8. The medical device of claim 1, wherein the ligature has a length that is sufficient to constrict or reduce a size of a heart valve.

9. The medical device of claim 1, wherein the ligature is flexible.

10. The medical device of claim 1, wherein a length of the ligature is smaller than a diameter of a heart valve.

11. The medical device of claim 1, wherein the ligature comprises one of a strap, a string, a cord, a wire, a thread, and a suture.

12. A medical device comprising:
    a ligature comprising an anchoring member at each end, the ligature of a size suitable to constrict or reduce a size of a valve of a heart and each anchoring member operable to couple to tissue and secure the ligature;
    a catheter coupled with the ligature and the catheter having a size suitable for percutaneous insertion through a blood vessel and the catheter operable to be maneuvered through the blood vessel to the heart, the catheter comprising a proximal end and a distal end and a lumen therethrough a distal portion of which is sized to accommodate the ligature;
    a delivery mechanism coupled to the proximal end of the catheter comprising a first deployment shaft to deploy a first anchoring member of the ligature and a second deployment shaft to deploy a second anchoring member of the ligature; and
    a handle coupled to the proximal end of the catheter, further comprising a first deployment mechanism and a second deployment mechanism, wherein the first deployment mechanism is configured for a dedicated deployment of the first anchoring member and the second deployment mechanism is configured for a dedicated deployment of the second anchoring member.

13. The medical device of claim 12, wherein each of the first deployment shaft and the second deployment shaft may be advanced beyond the distal end of the catheter.

14. A medical device comprising:
    a ligature comprising an anchoring member at each end, the ligature of a size suitable to constrict or reduce a size of a valve of a heart and each anchoring member operable to couple to tissue and secure the ligature;
    a catheter coupled with the ligature and the catheter having a size suitable for percutaneous insertion through a blood vessel and the catheter operable to be maneuvered through the blood vessel to the heart, the catheter comprising a proximal end and a distal end and a lumen therethrough a distal portion of which is sized to accommodate the ligature; and
    a delivery mechanism coupled to the proximal end of the catheter comprising a first deployment shaft to deploy a first anchoring member of the ligature and a second deployment shaft to deploy a second anchoring member of the ligature, wherein the delivery mechanism further comprises a first rotating mechanism and a second rotating mechanism wherein the first rotating mechanism can rotate the first anchoring member accommodated at the distal end of the catheter and the second rotating mechanism can rotate the second anchoring member accommodated at the distal end of the catheter.

* * * * *